(12) United States Patent
Baek et al.

(10) Patent No.: US 8,352,417 B2
(45) Date of Patent: Jan. 8, 2013

(54) SYSTEM, METHOD AND PROGRAM PRODUCT FOR MANAGEMENT OF LIFE SCIENCES DATA AND RELATED RESEARCH

(75) Inventors: Ock Kee Baek, Unionville (CA); Carl Stephen Ewig, San Diego, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 13/168,365

(22) Filed: Jun. 24, 2011

(65) Prior Publication Data
US 2011/0313809 A1 Dec. 22, 2011

Related U.S. Application Data

(63) Continuation of application No. 10/973,959, filed on Oct. 25, 2004, now abandoned.

(30) Foreign Application Priority Data

Oct. 31, 2003 (CA) .................................. 2447963

(51) Int. Cl.
G06F 7/00 (2006.01)
G06F 17/00 (2006.01)
(52) U.S. Cl. .................................................. 707/603
(58) Field of Classification Search .................. 707/603, 707/999.001
See application file for complete search history.

(56) References Cited

U.S. PATENT DOCUMENTS
2002/0152216 A1 10/2002 Bouthors
2002/0198751 A1 12/2002 Ernest et al.
2002/0198858 A1* 12/2002 Stanley et al. .................. 706/50

FOREIGN PATENT DOCUMENTS
JP 7271798 3/1994

OTHER PUBLICATIONS

Nguyen et al., "Integration of Temporal Reasoning and Temporal-Data Maintenance into a Reusable Database Mediator to Answer Abstract, Time-Oriented Queries: The Tzolkin System," Jul. 1, 1999, 121-145.*
Logical Operational Model: Life Sciences Informatics Reference Architecture Mar. 2000.
Stephen Fenstermaker et al., "METRICS: A System Architecture for Design Process Optimization" p. 705-710 UCLA Computer Science Dept.

(Continued)

Primary Examiner — Aleksandr Kerzhner
(74) Attorney, Agent, or Firm — Christopher & Weisberg, P.A.

(57) ABSTRACT

A system, method and program product for managing data for researchers. A research data server receives and manages experimental data and research data and results from the researchers, and operates with a virtual storage device to maintain the experimental data and research data and results. A reference data access server receives and manages external reference data relating to the research and operating with the virtual storage device to maintain the external reference data. Computational resources allow researchers to capture, process and analyze experimental data to obtain results. A research data network connects the virtual storage device, research data server, reference data access server and the computational resources to allow transfer of data there between. Security management services authenticate and authorize access by the researchers to the system.

17 Claims, 25 Drawing Sheets

OTHER PUBLICATIONS

Galis et al., Proceedings of the SPIE, The International Society for Optical Engineering, "Towards Multi-Domain Integrated Network Management for ATM and SDH Networks", SPIE vol. 2953, pp. 270-279 (1999).

Alex Galis, "Broadband Connectivity Management Service for Multi-Domain ATM and SDH Networks," Enterprise Applications and Services, University of London, pp. 1-8.

Jun-jang Jeng, "An Approach to Designing Reusable Service Frameworks via Virtual Service Machine," p. 58-66.

Mike Jude, "Network Management Tools and Trends" Business Communications Review, pp. 1-4, May 2002.

L. LeBlanc—Internet-enabled Technology Moves Batch Enterprises Towards New Growth, Higher Profits.

R. Neubert et al—Virtual Enterprises—Challenges from a Database Perspective IEEE 2001 0-7695-0960-6/01.

Ozawa et al—NIPPON—Method and Device for Evaluating Information Retrieving Method.

Nguyen et al., "Integration of Temporal Reasoning and Temporal-Data Maintenance into a Reusable Database Mediator to Answer Abstract, Time-Oriented Queries: The Tzolkin System," Journal of Intelligent Information Systems 13, pp. 121-145 (1999).

* cited by examiner

SYSTEM, METHOD AND PROGRAM PRODUCT FOR MANAGEMENT OF LIFE SCIENCES DATA AND RELATED RESEARCH

CROSS-REFERENCE TO RELATED APPLICATION

This application is a continuation of patent application Ser. No.: 10/973,959, filed Oct. 25, 2004, now abandoned entitled SYSTEM, METHOD AND PROGRAM PRODUCT FOR MANAGEMENT OF LIFE SCIENCES DATA AND RELATED RESEARCH, which claims priority to Canadian Patent Application No: 2,447,963, filed Oct. 31, 2003, the entirety of which both are incorporated herein by reference.

STATEMENT REGARDING FEDERALLY SPONSORED RESEARCH OR DEVELOPMENT n/a

FIELD OF THE INVENTION

The present invention relates generally to computer management of data and related research results. In particular, the present invention relates to a system, method and program product for computer management of data and related research for researchers in life science fields.

BACKGROUND OF THE INVENTION

Modern life sciences research, such as pharmaceutical research, typically requires applied, iterative, parallel research across many technical disciplines. Modern pharmaceutical research typically involves researchers from biology, genetics, chemistry, clinical and pathology disciplines. The research process is typically iterative, with the results from one discipline being supplied to another discipline, etc. with each discipline analyzing processing the supplied and other data. Heretofore, there have been inadequate computer systems and methods for collaboration between researchers in the different disciplines, and management of the overall process. These problems are exacerbated when large amounts of data are generated and must be transformed, translated, reorganized, analyzed or otherwise processed as the data moves between disciplines and/or research teams.

An object of the present invention is to provide an improved, comprehensive system, method and program product for collaboration among researchers and management of data and related research results.

Another object of the present invention is to provide a system, method and program product of the foregoing type which is suited for development of pharmaceuticals and other medical therapies.

SUMMARY OF THE INVENTION

The invention resides in a system, method and program product for managing data for researchers. Research data is automatically received from laboratory instruments. Established reference data is accessed from a database. Recently available reference data is automatically obtained. Experimental data is accessed from a database. There are a plurality of applications to process respective types of the data. In response to a request by a researcher to perform a data processing function, one or more of the processing applications are invoked and supplied with parameters to perform the data processing function. The one or more applications automatically access types of the data required to perform the respective data processing function.

According to features of the present invention, the determination of which of the processing applications to invoke and which parameters to supply to these processing applications can be based on a type of function requested by the researcher. The determination of the identities of files containing the data required by the one or more applications can be based on a type of function requested by the researcher. There can also be an application to analyze patterns in respective types of the data, and one of the processing applications receives from the pattern analyzing application a pattern used to perform the requested data processing function. There can also be a program for determining if available data is valid. If not, the available data is not used for the one or more processing applications. If so, the available data is used for the one or more data processing applications. There can also be a program for formatting results of the one or more data processing applications to correspond to respective types of data processing requests.

According to another embodiment of the present invention, there is provided another system for managing data for researchers. This other system comprises a virtual storage device including online and near line storage and having policies predefined for moving stored data between the online and near line storage. The system also comprises a research data server for receiving and managing experimental data and research data and results from the researchers and operating with the virtual storage device to maintain the experimental data and research data and results. The system also comprises a reference data access server receiving and managing external reference data relating to the research and operating with the virtual storage device to maintain the external reference data. The system also comprises computational resources for the researchers to capture, process and analyze experimental data to obtain results. The system also comprises a research data network connecting the virtual storage device, research data server, reference data access server and the computational resources to allow transfer of data there between. The research data network further includes security management services to authenticate and authorize access by the researchers to the system.

This other system may also include a data import controller connected to one or more public data networks (e.g., the Internet) as well as to the research data network. The data import controller is operable to retrieve external reference data from data sources external to the research data network according to one or more policies predefined by the researchers for retrieving external reference data. Also, the computational resources may include a high performance computing server comprising a cluster of homogeneous or hybrid computing resources. Also, the system may include a laboratory information management system connected to the research data network and to one or more laboratory instruments. The laboratory information management system receives experimental data from the laboratory instruments and provides that data to the research data server via the research data network.

According to another aspect of this other embodiment of the present invention, there is provided a method of managing data for research. A set of policies defining external reference information relevant to the research program is created. At predefined intervals, external reference information in accordance with the policies is retrieved. The retrieved information is compared with reference data stored in a reference data server to determine if the retrieved information is redundant or of lower quality than data already stored in the reference data server. The retrieved information which was determined to be non-redundant and/or of acceptable better quality is stored in the reference data server. The experimental data from optionally one or more laboratory instruments is stored in a research data server. The researchers are provided with access to the stored information in the reference data server and to experimental data in the research data server.

According to yet another aspect of the present invention, there is provided a method of managing data for research. Researchers are provided with access to a research data network. Reference data policies define for each researcher types of reference data that will be of use to the researcher. Experimental data policies define for each researcher types of experimental data and results that will be of use to the researcher are created and stored on the research data network. At defined intervals, from data sources outside the research data network, external reference data as defined by the reference policies is retrieved and examined to determine if it is redundant in view of reference data already stored on the research data network or if it is of better quality than reference data already stored on the network. The retrieved reference data which has been determined to be non-redundant or of better quality than reference data already stored is stored on the research data network. Experimental data is collected from laboratory instruments through the research data network and stored on the research data network. New reference data and experimental data are published to researchers according to the reference data policies and experimental data policies defined for the researchers.

According to yet another aspect of the present invention, there is provided a computer program product stored on a computer readable medium to manage data for research. First program instructions provide the researchers with access to a research data network. Second program instructions retrieve, at defined intervals, from data sources outside the research data network, external reference data as defined by reference policies created on the computer by researchers. Third program instructions examine the retrieved reference data to determine if it is redundant in view of reference data already stored on the research data network or if it is of better quality than reference data already stored on the network, and store retrieved reference data on the research data network which has been determined to be non-redundant or of better quality than reference data already stored. Fourth program instructions store experimental data from optionally one or more laboratory instruments in a research data server. Fifth program instructions provide the researchers with access to the stored information in the reference data server and to experimental data in the research data server.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

While the following embodiment illustrates use of the present invention for pharmaceutical research, the present invention has other embodiments and uses as well. For example, the present invention can be employed in research for pharmaceuticals, treatments, diagnostics, non-drug treatment protocols and preventatives, and other sciences.

Modern life sciences research, such as high level drug discovery and development, comprises a series of steps for acquiring and analyzing chemical and biological data, wherein processing is performed at each step. For example, in the high-level drug research areas, the key activities typically include (a) the collection of "assay" data generated by laboratory instruments, (b) searching for and obtaining external reference and research materials, (c) analyzing the consolidated assay data and the external reference materials, and (d) deriving knowledge through the analysis. These tasks are typically repeated, in a cyclical manner, by each discipline within the research team. The present invention assists in these key activities, providing automation, data management and multidisciplinary collaboration facilities between researchers in different disciplines.

Figure 1:
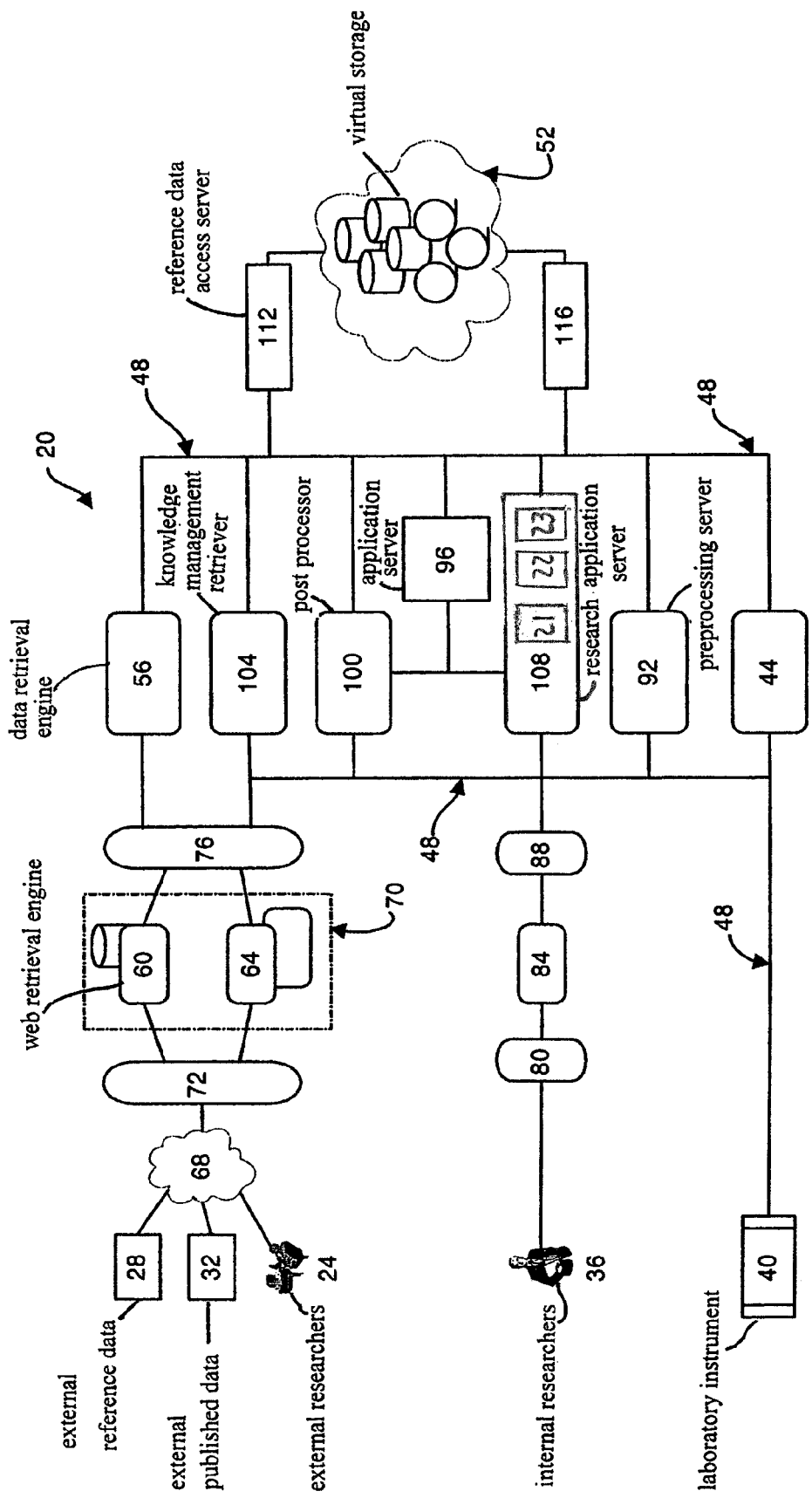
FIG. 1 is a block diagram of a computer system in accordance with the present invention.

In FIG. 1, a system in accordance with the present invention is indicated generally at 20. System 20 interfaces with external researchers 24, external data sources such as external reference data 28 and external published data 32, internal researchers 36 and laboratory instruments 40. As explained above, modern life sciences research often involves the exchange of information with various external researchers 24 who are not members of the primary research organization. Examples of such external researchers may be government funded researchers, such as researchers funded by the U.S. National Institutes of Health, researchers affiliated with Contract Research Organizations (CRO), etc. While FIG. 1 only shows a single icon for external researchers 24, the present invention supports interaction with multiple external researchers 24 at disparate geographic locations and at disparate organizations. Access to and use of external reference data 28 and external published data 32 is often an important part of a life sciences research effort.

External reference data 28 can comprise well known or established gene sequence and protein databases, either public or private, clinical data, etc. External published data 32 can include newly discovered genes or proteins, novel drug targets such as novel chemical entities or novel molecular entities, new insights in disease mechanisms, etc. The external published data 32 may reside in a known database, such as the PubMed database which is maintained by the National Center for Biotechnology Information. The relevant published data an be periodically identified and retrieved automatically by the data retrieval engine 56 by key word searching or author searching, based on predefined key words and authors.

Internal researchers 36 are primary drivers of the current research effort. While FIG. 1 only shows a single icon for internal researchers 36, the present invention supports interaction with multiple internal researchers 36 who can be part of different groups involved in the research effort and/or who can be located at disparate logical and/or geographic locations.

Laboratory instruments 40 can include any instrument useful to the research effort. In the life sciences field, such instruments can include gene sequencers, mass-spectrometers, crystallographic imaging devices, tomographic equipment, etc. Many such instruments are now robotic in nature and can directly interface with a laboratory information management system (LIMS) 44. An example of such an instrument is an ABI DNA sequencing system which directly interfaces to LIMS 44 and to one or more personal computers in the laboratory which provide for control and/or calibration of the device. Other instruments require manual operation and/or examination of their results by a technician or researcher, but these results are still provided to LIMS 44 for the assays. LIMS 44 are well known in the life sciences field and can be custom designed for a laboratory or can be purchased commercially, as desired.

As shown in FIG. 1, LIMS 44 is connected to instruments 40 by a research data network 48 which also connects the other components of system 20. Network 48 is not particularly limited; all components of system 20 should be able to communicate as necessary and, preferably, at a sufficient speed to allow effective transfer of information between various nodes connected by the network. Network 48 can be, for example, (a) a homogenous network of gigabit Ethernet links and network devices, (b) a heterogeneous network of, for example, fiber optic, gigabit Ethernet and ATM links with appropriate bridges, protocol converters, etc., (c) a private, operated and maintained for or by a research organization, (d) or a mix of private and public network portions separated and/or protected as required by appropriate firewalls, domain controllers for directory, security and system management services and encryption/decryption engines.

The data stored and used by system 20 is classified as follows for subsequent processing by research applications, as explained below. The external reference data 28 is classified by type based on the data file in which the external reference data resides. When a unit of external reference data 28 is identified as a candidate to be included in a data file, a data manager (person) determines the type of the candidate external reference data and stores it in the data file that is earmarked for this type of data. (Alternately, a program tool can search each unit of external reference by key word, and classify the external reference data based on the results of the key word search.) The web retrieval server 56 classifies each item of external published data 32 by type based on key words found in the publication. The type of data obtained from the LIMS is based on the type of instruments that are generating the data. Each of the classification types is one of a multiplicity of predetermined types. These types were predetermined by one or more scientists with expertise in such classification and research applications that will need the data. As explained in more detail below, each research application will need and fetch certain types of data to be processed on behalf of a researcher. Each data item can also be accompanied by a header file which indicates whether the data needs to be preprocessed (such as by preprocessing server 92 shown in FIG. 1), whether the data needs to be routed to a data mining application (such as data mining application 290 shown in FIG. 8), and the format of the data needed for the type of end user/researcher.

System 20 also includes a virtual storage device 52. As mentioned above, life sciences research can produce large quantities (petabytes or exabytes) of data. System 20 employs virtual storage device 52 to facilitate the handling of this data. Virtual storage device 52 comprises a collection of online storage devices, such as disk drives, solid state drives, etc. and a variety of near line storage devices, such as robotic tape libraries, etc. which can retrieve requested data within about one minute. Virtual storage device 52 employs a set of policies to manage the storage of research data sets between the online and near line storage subsystems. Such policies can employ strategies such as automatic migration of aged data from online to near line storage, heuristic migration based upon determined usage patterns for the data, etc. Because storage device 52 is virtual, it can be scaled as necessary by adding more storage devices. Also, it is transparent to a user whether desired data is stored in online or near line storage, although in the case of data stored on near line storage, the user may experience a slight delay in access. By way of example, virtual storage device 52 for current research efforts has at least several terabytes of online storage and several petabytes of near line storage. An example of a suitable virtual storage device 52 would be one or more IBM Enterprise Storage Servers and one or more IBM LTO UltraScalable Tape Libraries. In system 20, virtual storage device 52 stores all research data relating to a research effort, although local copies of smaller data sets can be maintained by researchers. By employing virtual storage device 52 across system 20, quality, integrity, security, privacy and availability of research data is assured.

Data retrieval engine 56 operates with a web retrieval engine 60 to retrieve (based on predefined key word search and predefined author search policies) and process desired external reference data over public networks such as the Internet 68. Specifically, a data retrieval engine 56 in the form of a data import controller uses these policies established by the research team to have web retrieval engine 60 retrieve external data. Web retrieval engine 60 processes the policy-driven requests from data import controller 56 to automatically retrieve predefined external reference data through the Internet 68, or other networks, via appropriate protocol and/or data format converters. Policies for web retrieval engine 60 can include regularly scheduled searches of specific databases, identification and retrieval of updated versions of previously retrieved data, searches for new data sources, etc. Examples of suitable web retrieval engines are the IBM WebSphere software platform or Apache Software Foundation web server integrated with the IBM WebSphere platform. Web retrieval engine 60 can use any appropriate computer program to retrieve the desired external references, such as ftp for document transfers, SQL queries for database searches, etc. In one embodiment of the invention, web retrieval engine 60 includes local storage where retrieved information is temporarily stored, for subsequent processing by data import controller 56.

B2B engine 64 includes a web server and operates to make data from system 20 available to external researchers 24. Examples of suitable B2B web retrieval engines 64 also are the IBM WebSphere software platform or Apache Software Foundation server integrated with IBM WebSphere platform. As discussed below, system 20 includes security management services which operate to limit the data that can be accessed by an external user 24.

As illustrated in FIG. 1, both web retrieval engine 60 and B2B engine 64 are located in a "demilitarized zone" (DMZ) 70 and are separated from network 48 and public networks such as Internet 68 by a protocol firewall 72 and a domain firewall 76. Protocol firewall 72 operates as a first line of isolation and acts to control the direction of data flows between network 48 and public networks such as Internet 68 and filters the data traffic flow based upon source addresses, destination addresses and enabled ports. Domain firewall 76 acts as a second line of isolation and establishes the DMZ between the trusted internal network 48 and external networks, such as Internet 68. Protocol firewalls 72 and domain firewalls 76 and other techniques for establishing DMZ's are well known and well not be further discussed herein. In a similar manner, system 20 connects internals researchers 36 through an internal DMZ formed by a protocol firewall 80, a web server 84 and domain firewall 88. Examples of suitable web engines are the IBM WebSphere software platform or an Apache Software Foundation server integrated with the IBM WebSphere platform.

System 20 also includes a preprocessing server 92 which comprises one or more computer systems. Preprocessing server 92 operates on the raw data provided by LIMS 44 to convert that data into data which is chemically, biologically, clinically etc. useful and relevant for the purpose and context of the research. Depending upon the nature of the assay and the devices performing the assay, this preprocessing can include data filtering, data normalization, data validation, etc. For example, preprocessing server 92 can filter data by removing a data set with key missing values, or data with noisy or statistically improbable values, such as long nucleotide segments in which all bases are identical. For example, preprocessing server 92 can normalize data by establishing a common scale or set of units for comparing disparate data, such as by multiplying the data by a constant to make the maximum value in each set precisely 1.0. For example, preprocessing server 92 can invalidate data which falls outside of certain expected data ranges, or is inherently invalid, such as ovarian cancer found in a man. Preprocessing server 92 can also assign a higher reliability to data which has previously been reviewed and annotated by a researcher.

System 20 includes an application server system 96 which includes a high performance computing server (HPCS). In a presently preferred embodiment, the HPCS comprises a high performance computing cluster, such as a Linux cluster of high speed processors, as this allows a large amount of available computing resources to be scaled appropriately, as needed, by adding or removing computing processors to and from the cluster. Gene multiple sequence alignment and/or protein folding are just a few examples of research activities which can require large amounts of computing resources. The HPCS is capable of serving as a back end processing resources for several research applications. As explained in more detail below, application server system 96 also includes a data mining application 292 and research applications 282, 284 and 286.

System 20 also includes a post processor 100 to operate on results produced in application server system 96, or elsewhere, to convert resultant data into chemically, biologically, etc. useful forms which are relevant for the purpose and context of the research. This post processing can comprise data clustering, annotation, classification, presentation, etc. and can be performed by various applications.

System 20 also includes a knowledge management server (KMS) 104. KMS 104 provides the researchers with access to relevant biological, chemical and/or clinical information. The functions provided by KMS 104 can include, without limitation, data mining, ad hoc queries, statistical analysis, report generation, decision support, etc. An example of a suitable knowledge management server 104 can include an IBM Information Management for Scoring, Visualization, Modeling and Mining.

RAS 108 may include a computer-readable tangible storage device 21, processor 22 and random-access memory (RAM) 23 in which a computer program or computer application is stored in computer-readable tangible storage device 21 for execution by processor 22 via RAM 23. For the sake of clarity, other computer-readable tangible storage devices, processors and RAMs have been omitted from other servers and computer devices illustrated in FIGS. 1-8. It is understood, however, that these elements are present the servers and computer devices illustrated in FIGS. 1-8. System 20 also includes a research application server (RAS) 108. RAS 108 runs a number of research applications, data mining applications and/or other tools required by researchers. These applications, data mining applications and/or tools can include, without limitation: an NCBI Basic Local Alignment Search Tool ("Blast") program, multiple sequence alignment tools, gene expression applications, and applications for protein structure and function prediction. The Blast program is a search tool to determine the similarity of a given nucleic acid or protein sequence to thousands of other sequences in databases, such as NCBI databases. The multiple sequence alignment tools assist in deducing the function of new proteins, assisting in answering other biological questions such as the evolution and/or phylogenic relationship of the protein. The gene expression applications permit interactive retrieval and analysis of gene expression data with spotted microarray, high density oligonucleotide array, hybridization filtering, serial analysis of gene expression data and other techniques. The applications for protein structure and function prediction include primary sequence alignment, secondary and tertiary structure prediction methods, homology modeling and crystallographic diffraction pattern analysis, etc. As will be apparent to those of skill in the art, many other applications and/or tools can be employed in system 20, and RAS 108 can provide for centralized maintenance and control of these tools.

System 20 also includes a reference data access server 112 and a research data server 116 which operate with virtual storage device 52 and data import controller 56. Reference data access server 112 allows researchers to access reference data, both external data and internal data, for ad hoc queries against a virtual database through federated access to the data sources. By way of example, the virtual database system in reference data access server 112 can be the IBM DiscoveryLink middleware application and the IBM DB2 Universal Database, although other suitable techniques and/or applications can be used. The DiscoveryLink application allows an ad hoc query against multiple data sources in a single request and provides a single response, regardless of geographic locations of data sources, types, formats, schemas and operating platforms, network protocols, etc. External reference data (for example, genome, EST, protein and/or clinical databanks) can be consolidated, using replication, into one logical location to mitigate accessing external reference data through slow, external links such as Internet 68. Using local replicas of reference data provides significant advantages over using the original external sources, although provision must be made to maintain the currency of the external data and costs are incurred in providing the storage space for the local replicas. However, these issues are addressed via data import controller 56 and virtual storage device 52, as described above.

Research data server 116 allows various research applications to access consolidated research and/or experimental data. Examples of such research and/or experimental data include microarray data and serial analysis of gene expression data. Experimental data typically results from experiments performed by the same organization as employs the researcher which uses application server system 96. When a computer or other device generates the experimental data, the computer or other device automatically populates a database with the experimental data based on a configuration file within the computer. Examples of suitable research data servers 116 include the IBM Enterprise Storage System and the IBM Hierarchical Storage Management solutions.

In addition to the nodes, servers and other devices described above, system 20 also includes the following shared system services. Directory management provides naming services to registered entities (e.g.—users, applications, other resources, etc.). Security management provides services to protect assets and resources such as user/entity identification and validation/authentication, access control, privacy protection and security audit functions. System management in conjunction with client software running on managed devices/nodes, provides management services such as problem alerts/reports, performance monitoring, software distribution, data backup and recovery, etc. Storage management in conjunction with virtual storage device 52, provides integrated, consolidated and reliable data storage for reference data access, research data and experimental data.

Examples of the operation and use of system 20 in aspects of a research program will now be described.

Figure 2A:
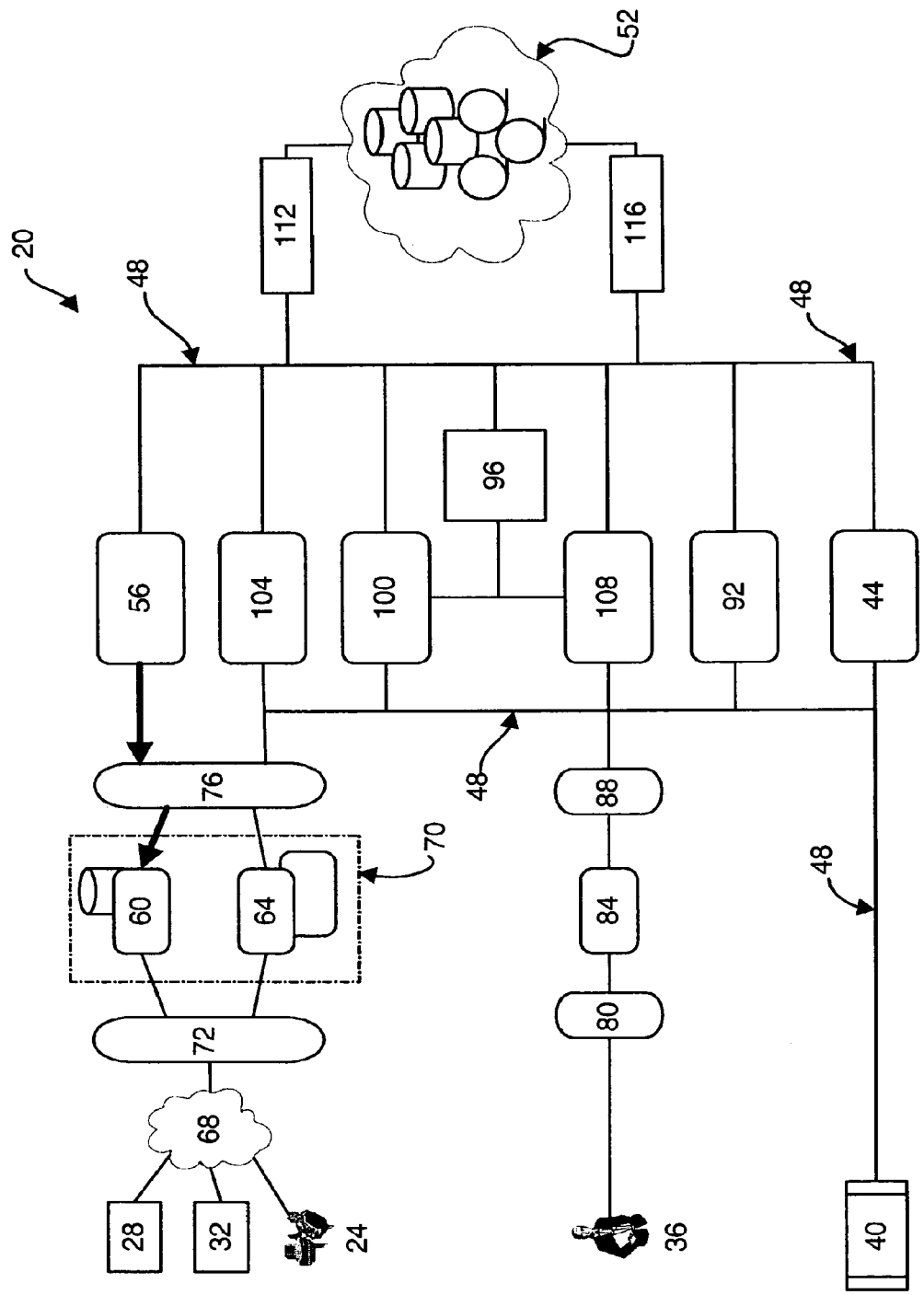
FIG. 2a shows control and data flows between components of the system of FIG. 1 when retrieving and processing external data and publications.
Figure 2B:
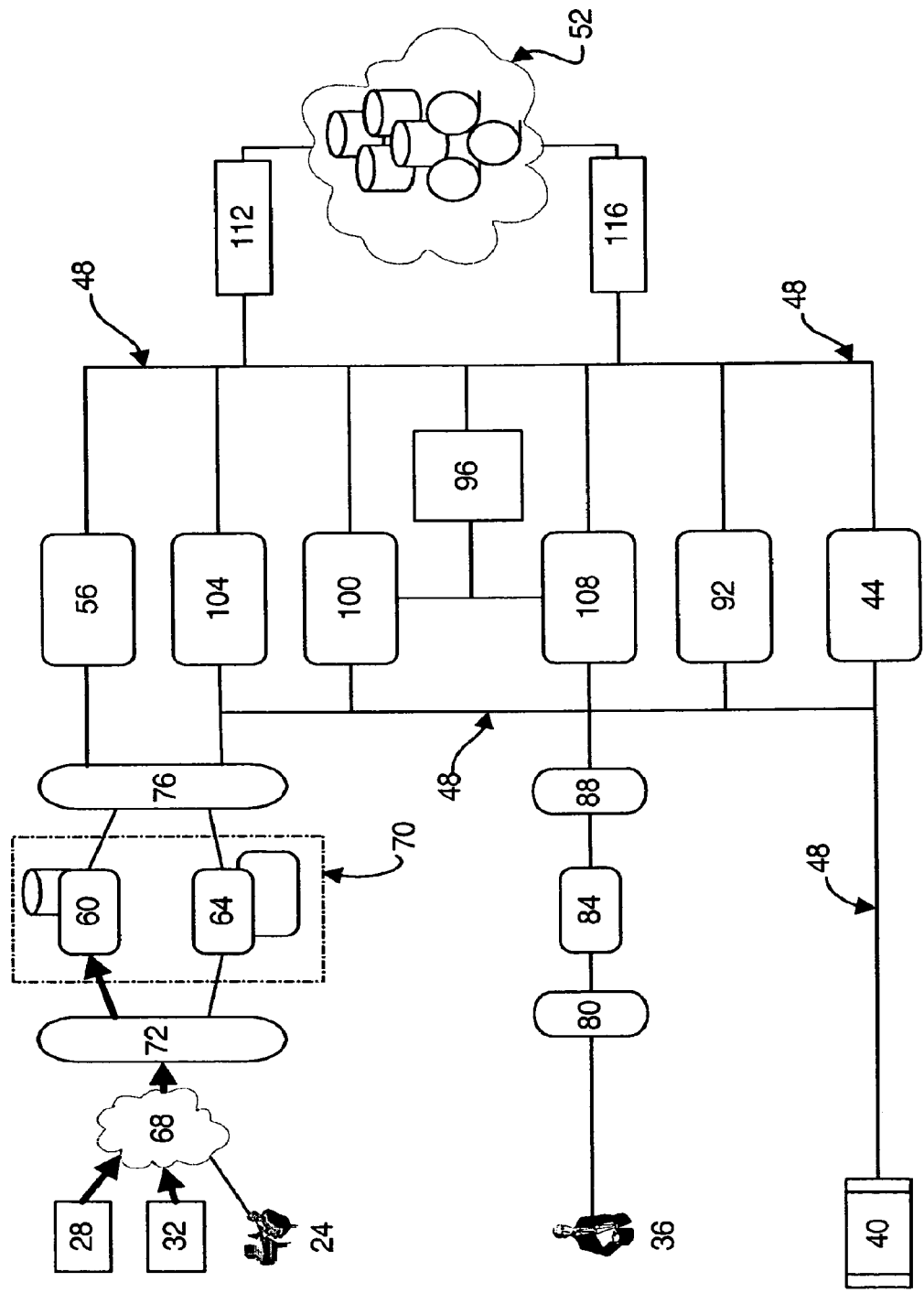
FIG. 2b shows control and data flows between components of the system of FIG. 1 when retrieving and processing external data and publications.
Figure 2C:
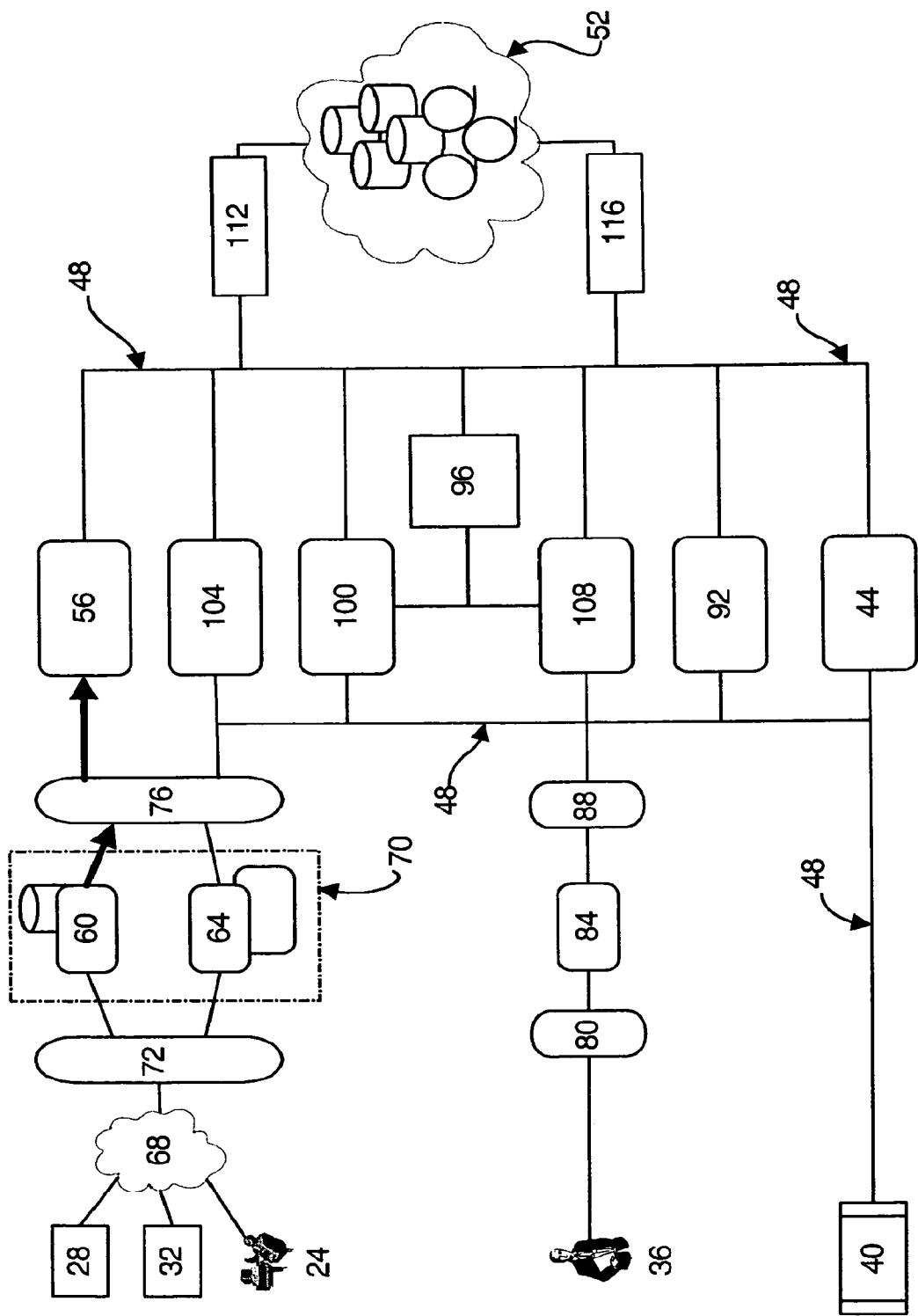
FIG. 2c shows control and data flows between components of the system of FIG. 1 when retrieving and processing external data and publications.
Figure 2D:
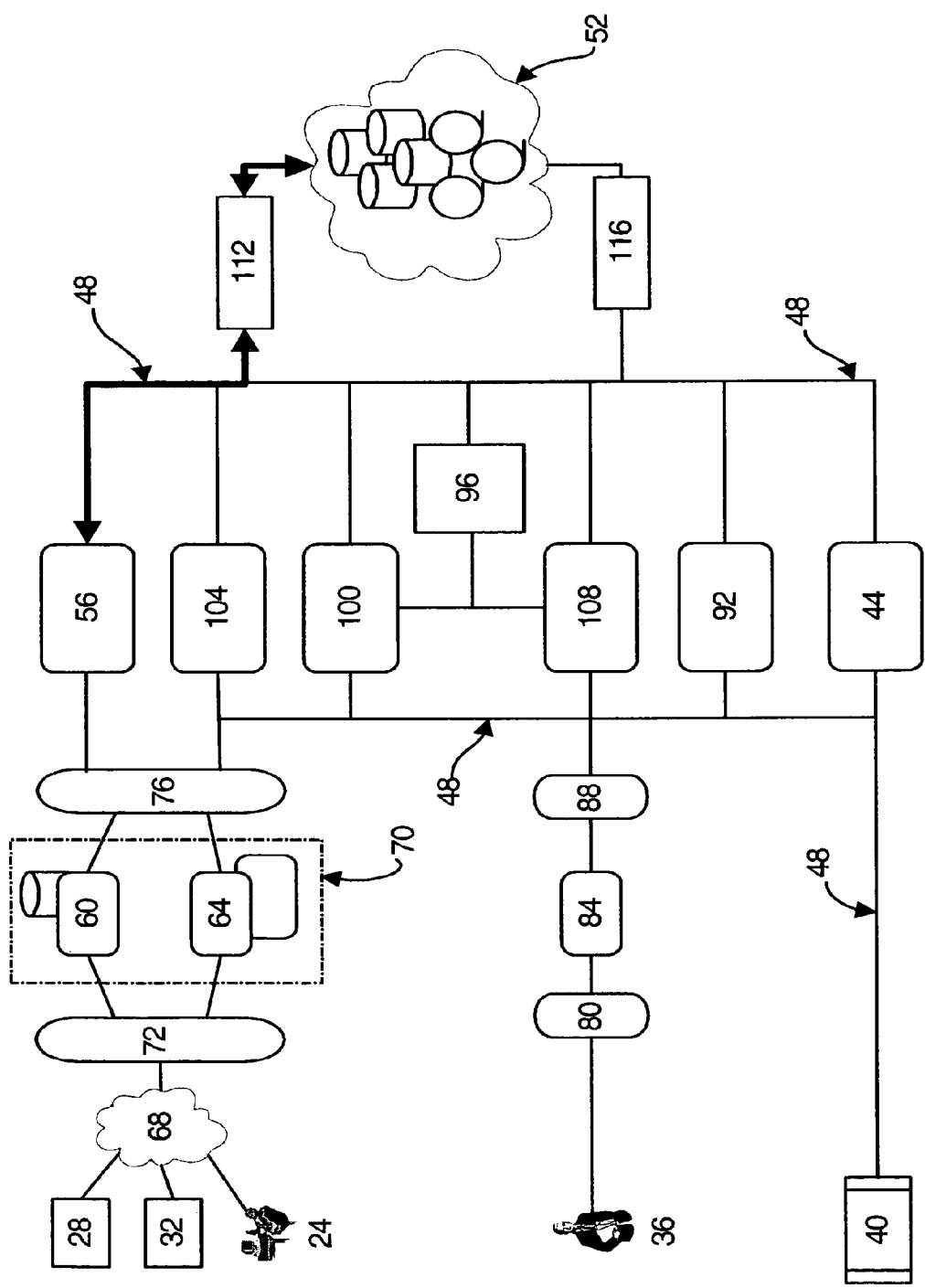
FIG. 2d shows control and data flows between components of the system of FIG. 1 when retrieving and processing external data and publications.

FIGS. 2a through 2e show an example of system 20 retrieving external data 28 and external published information 32 via Internet 68. In the first step, shown in FIG. 2a, data import controller 56, in accordance with the data retrieval policies established by the research team using system 20, instructs web retrieval engine 60 to retrieve the information. In FIG. 2b, web retrieval engine 60, which runs in external DMZ 70, retrieves the information from predefined sites on the Internet, such as GenBank, etc. and stores the retrieved information in the temporary local storage of web retrieval engine 60. For security, the session is initiated for an outbound session only and the data flows are inbound only through protocol firewall 72 and domain firewall 76. The retrieved information is not particularly limited and can include gene data, protein data, documents, abstracts, chemical data, etc. and will include both structured data (protein database) and unstructured data (academic papers/journals). If the nature of the retrieved information and data requires it, web retrieval engine 60 can scan for the presence of computer viruses and/or otherwise check the retrieved information and data for security issues. When the data has been retrieved and placed into temporary storage, web retrieval engine 60 forwards the information to data import controller 56, as shown in FIG. 2c. Data import controller 56 parcels the data into smaller and relevant data sets and then sends the data to the reference data access server 112 for quality checks, as shown in FIG. 2d.

Figure 2E:
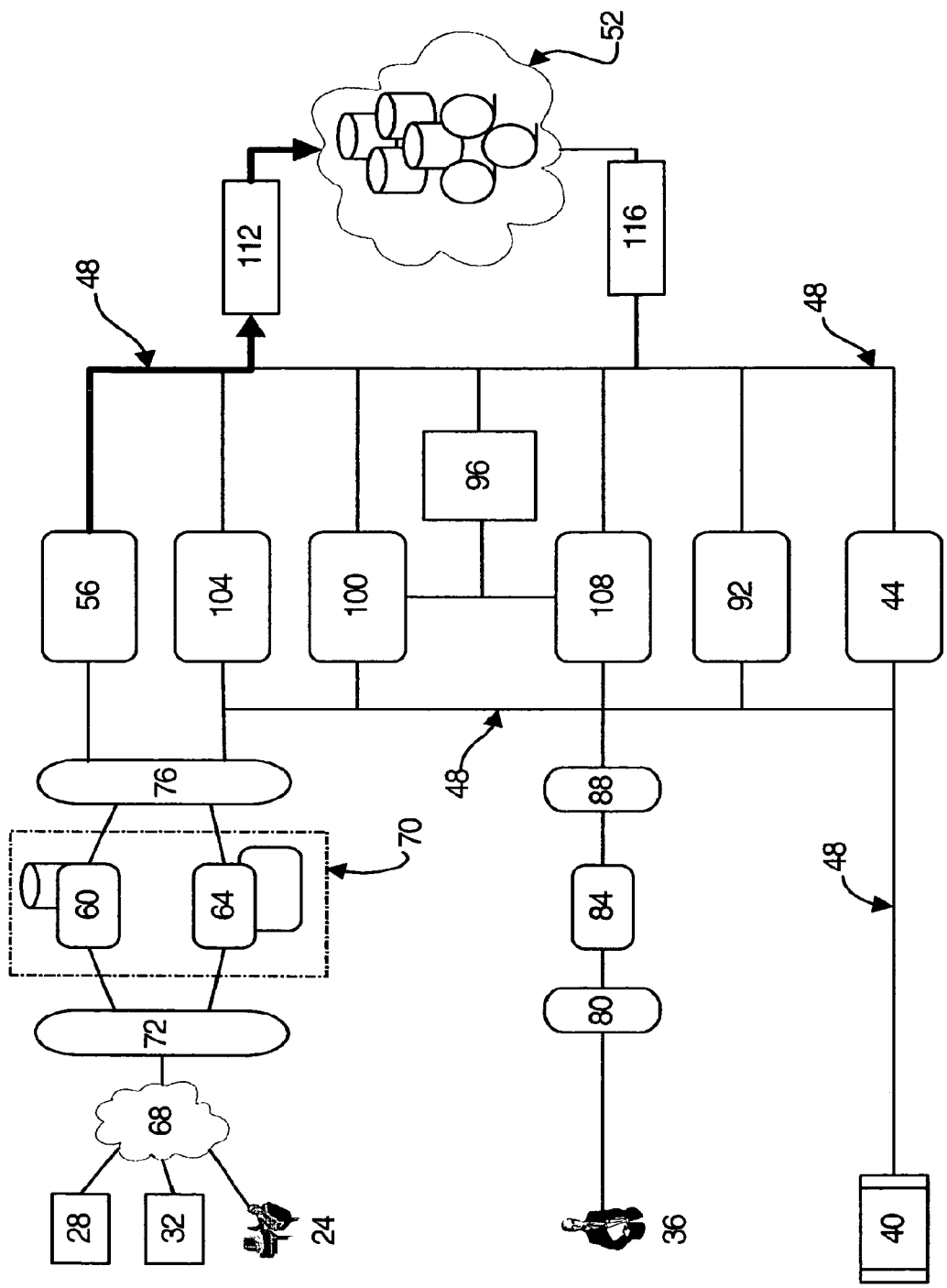
FIG. 2e shows control and data flows between components of the system of FIG. 1 when retrieving and processing external data and publications.
Figure 10:
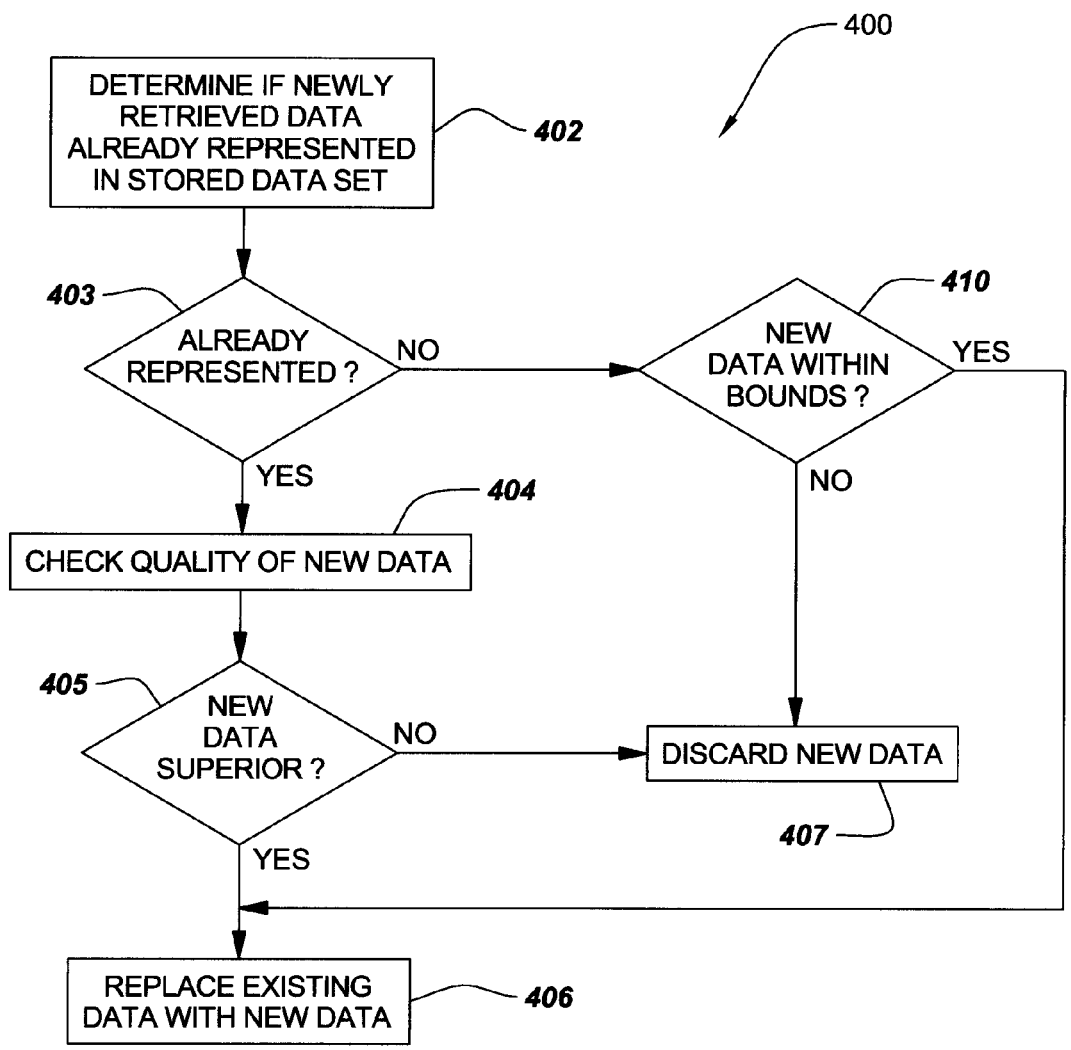
FIG. 10 is a flow chart showing a function within a reference data access server within the system of FIG. 1 to validate new external data.

As illustrated in FIG. 10, a program 400 running on the reference data access server 112 compares the retrieved, partially processed, data to the authoritative, non-redundant data sets stored in virtual storage device 52 (step 402). If newly collected data is already in the authoritative data sets (decision 403, yes branch), the program 400 checks the quality of the newly collected data to determine whether the newly collected data is superior to the existing data. "Superior" data is typically data which is input later in time, and not "out of bounds", i.e. is within constraints permitted for the data. For example, if the data states that the disease is ovarian cancer, and indicates that the patient is male, then the data is out of bounds. As another example, if the range of a certain biological chemical is one thousand ppm to two thousand ppm, and the measure for the new data is three thousand ppm, then it is out of bounds. If the newly collected data is superior (decision 405, yes branch), the existing data is replaced in virtual storage device 52 with the newly collected data and the meta data managed by the reference data access server 112 is updated accordingly (step 406). Otherwise, the newly collected data is deleted or marked inferior (step 407). Referring again to decision 403, no branch where the newly collected data is not already in the authoritative data sets, a check is made if the newly collected data is within bounds (step 410). If so, then the meta data stored in reference data access server 112 is accordingly updated (STEP 406), and the new data will be stored in virtual storage device 52, as shown in FIG. 2e, whether unique or redundant, to allow researchers to revisit and/or confirm the retrieved data in the future, should the need arise. If the new data is out of bounds (decision 410, no branch), then it is discarded (step 407).

Figure 3A:
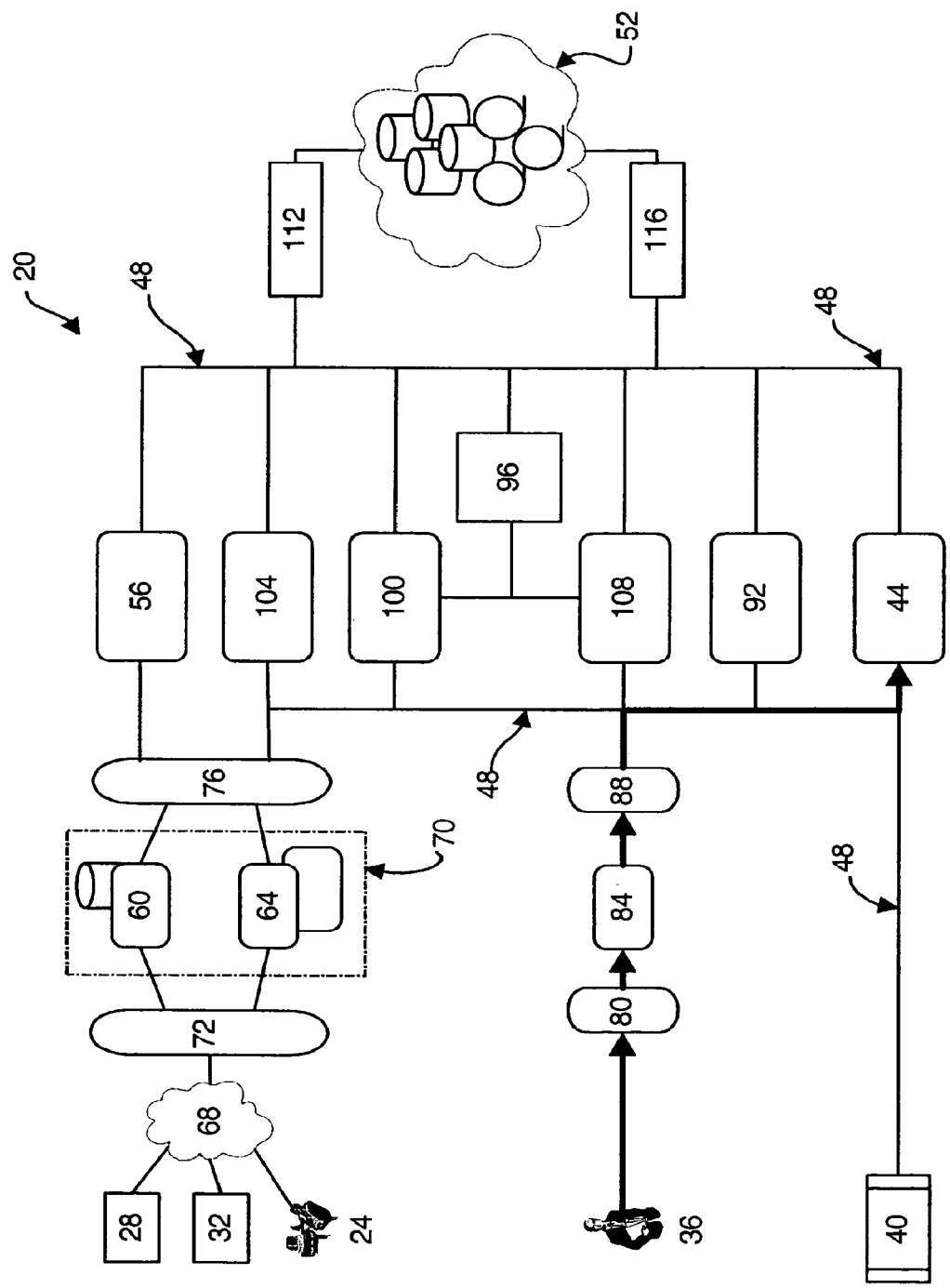
FIG. 3a shows control and data flows between components of the system of FIG. 1 when collecting experimental data from laboratory instruments.
Figure 3B:
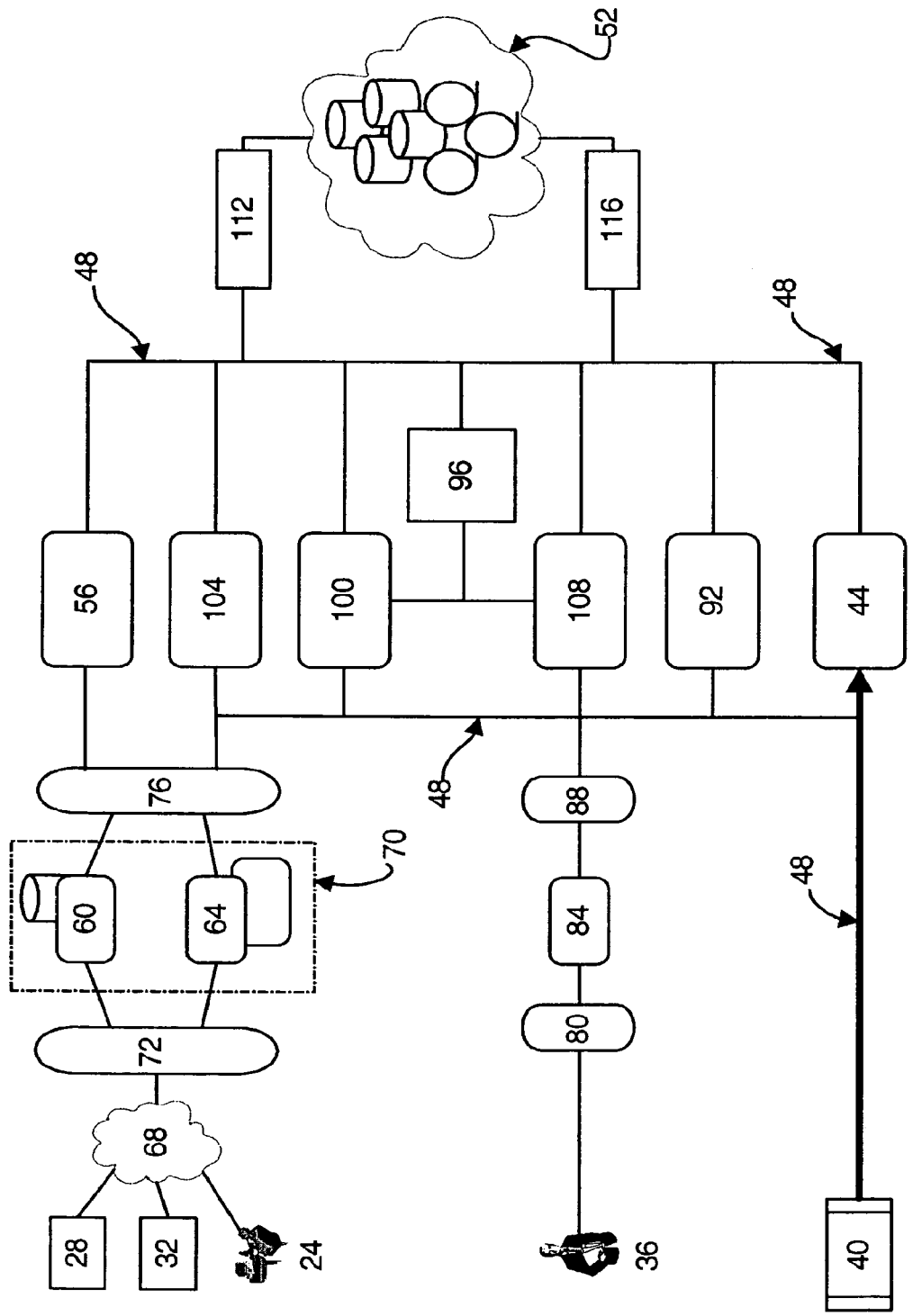
FIG. 3b shows control and data flows between components of the system of FIG. 1 when collecting experimental data from laboratory instruments.
Figure 3C:
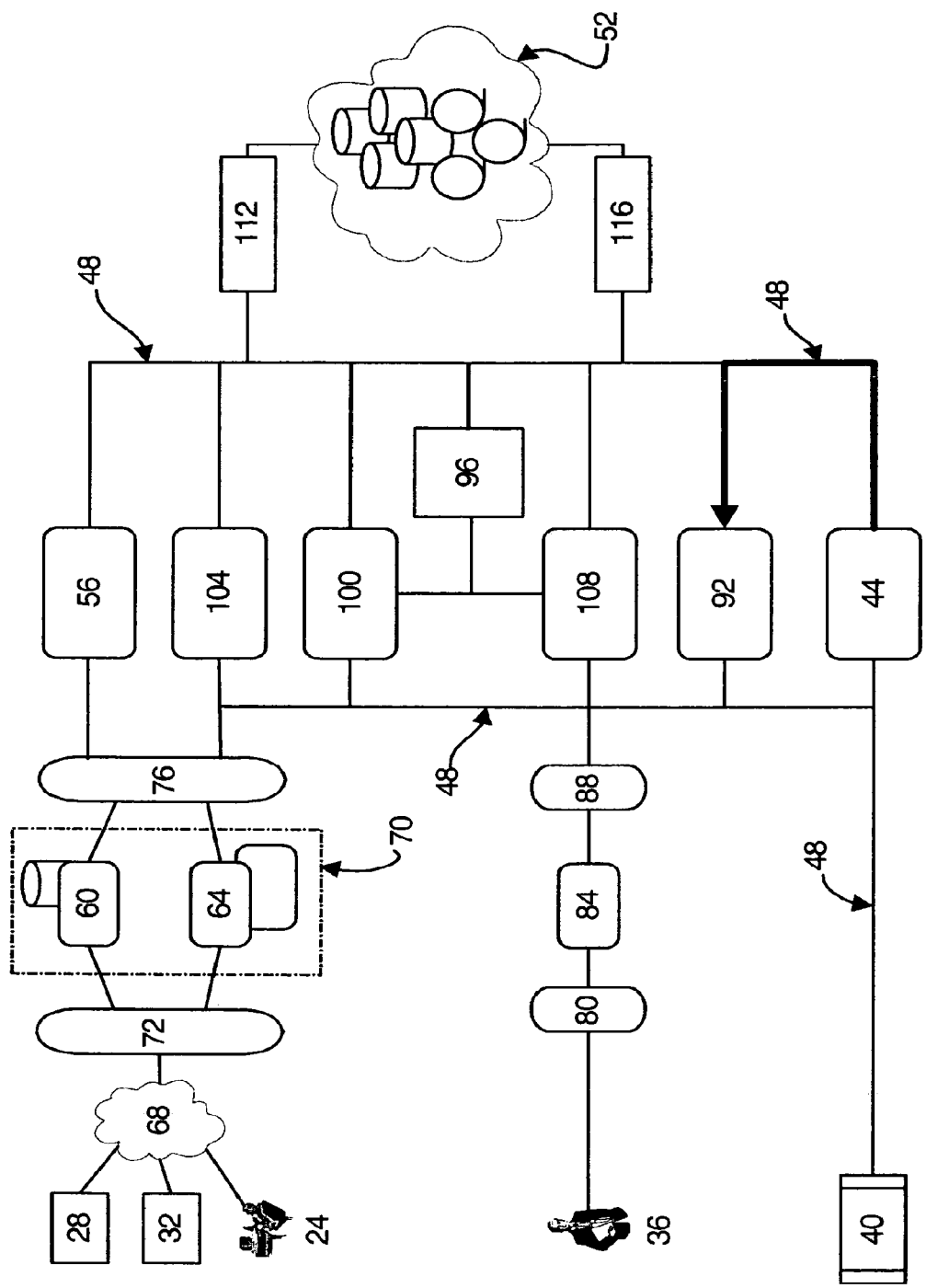
FIG. 3c shows control and data flows between components of the system of FIG. 1 when collecting experimental data from laboratory instruments.
Figure 3D:
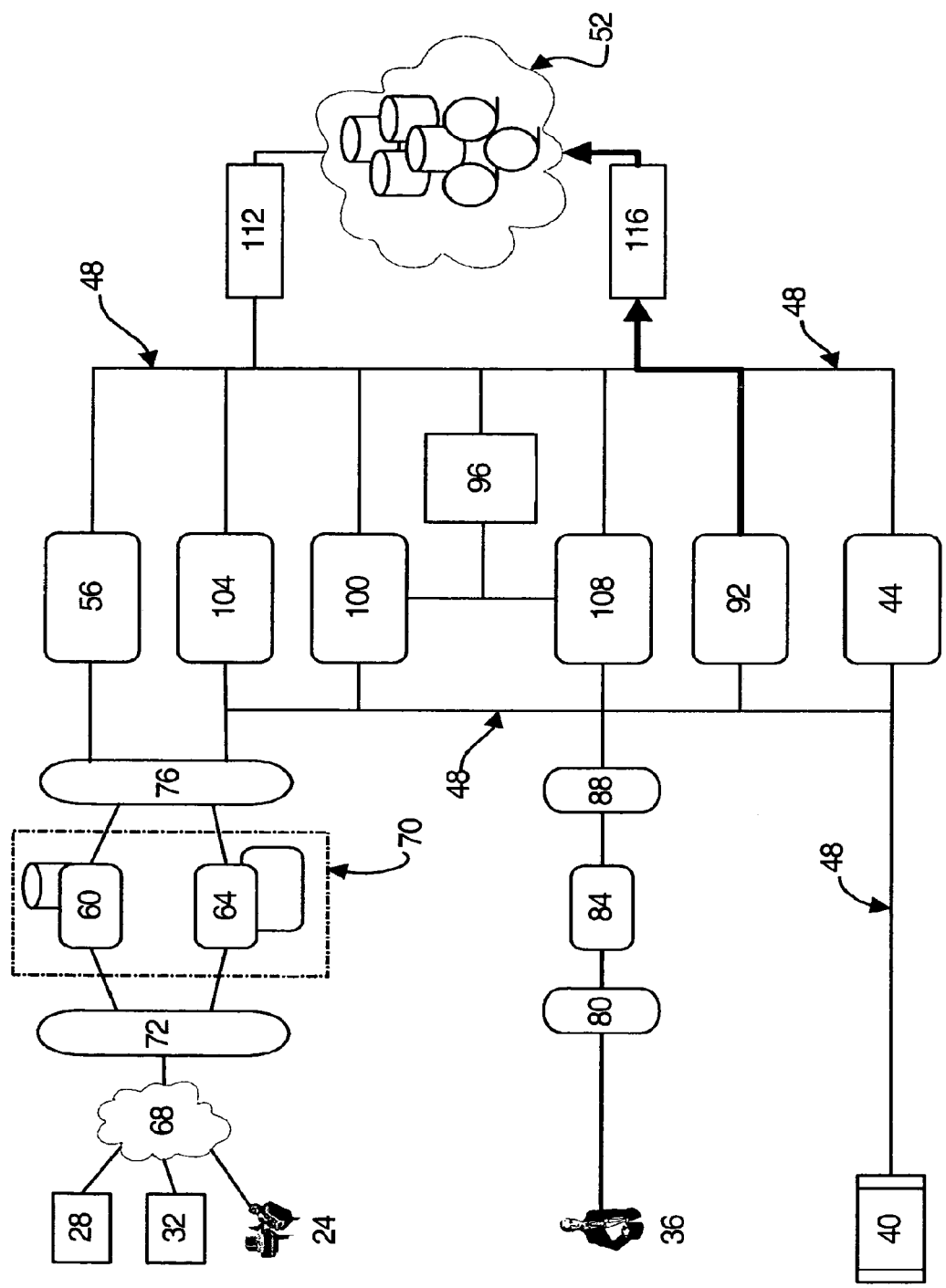
FIG. 3d shows control and data flows between components of the system of FIG. 1 when collecting experimental data from laboratory instruments.

FIGS. 3a through 3d show an example of collection of experimental data by system 20. In FIG. 3a, an internal researcher 36 interacts, via a personal computer or other interface device (not shown) with an appropriate web page served by web server 84 to input experimental conditions, experimental samples and other relevant information into LIMS 44. This session is authenticated and authorized by the security management services in system 20. As shown in FIG. 3b, the raw measured experimental data is provided to LIMS 44 from instruments 40, and LIMS 44 then merges the experimental data with the data input by the researcher 36. The merged data is then preprocessed, by preprocessing server 92 to filter and normalize the data to obtain a useful data set as shown in FIG. 3c. Referring to FIG. 3d, the filtered and normalized data set generated by reference data access server 112 is placed in research data sever 116 and stored in virtual storage device 52, where it will be initially stored in online storage and eventually moved to near line storage, in accordance with the storage policies defined for virtual storage device 52 by the research team.

Figure 8:
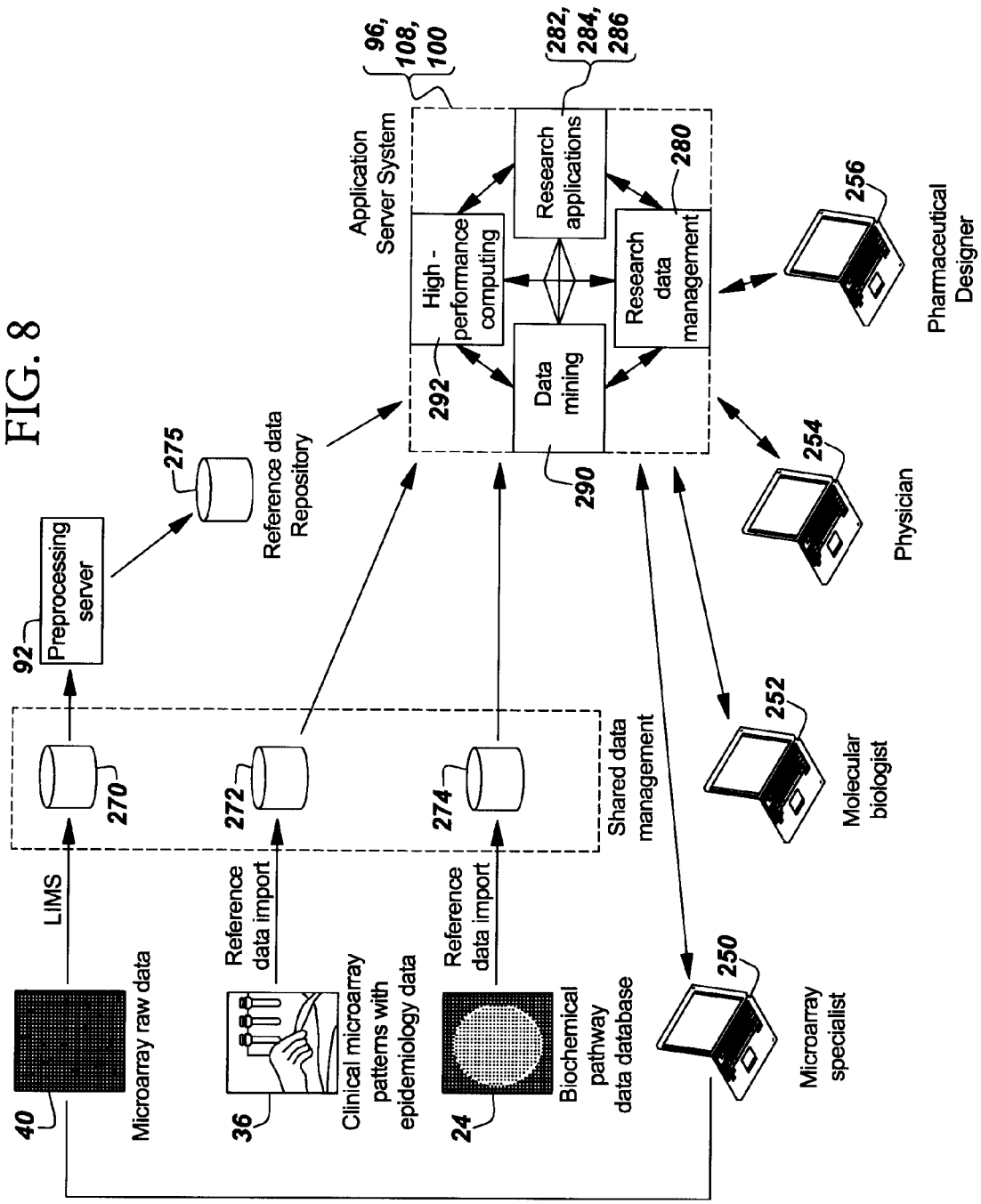
FIG. 8 is a flow diagram showing an example of the present invention.

FIG. 8 illustrates an example of preprocessing performed by server 92. Data is input from three sources, i.e. (1) an automated LIMS 40 controlling automated, high-throughput production of microarrays from a large number of fractionated tissue extracts, (2) clinical data, particularly the presence and severity of disease symptoms, and their associated microarray data, typically from specific affected tissues and optionally other epidemiological data from researchers 36, and (3) a database 28 or 32 of biochemical pathways, optionally focusing on specific types of pathways of interest. For sources 36, 28 or 32, the reference data import may be either local or remote over the Internet. As explained above, each piece of data has been classified as one of a multiplicity of predetermined types. In this example, the three types of data are assigned a common representation. Microarrays and biomolecular pathways may be described by two-dimensional matrices, clinical data by annotations to such matrices, and the combination of the three by a relational database.

The raw microarray data 40 is collected into a local repository 270, then sent to preprocessor server 92 to filter out missing data, to check for errors such as smearing of the spots, and usually to perform a cluster analysis to group rows and columns that display similar colors and intensities. The result would typically be the standard Clustered Image Map (CIM) representation, which is stored in a reference repository. In parallel, clinical data 36 may be obtained in a standard representation, such as HL7 and CDISC and stored in a local repository 272. Also in parallel, one or more databases of biochemical interaction data 24, such as the STKE database, are accessed and stored in a local repository 274.

Figure 9:
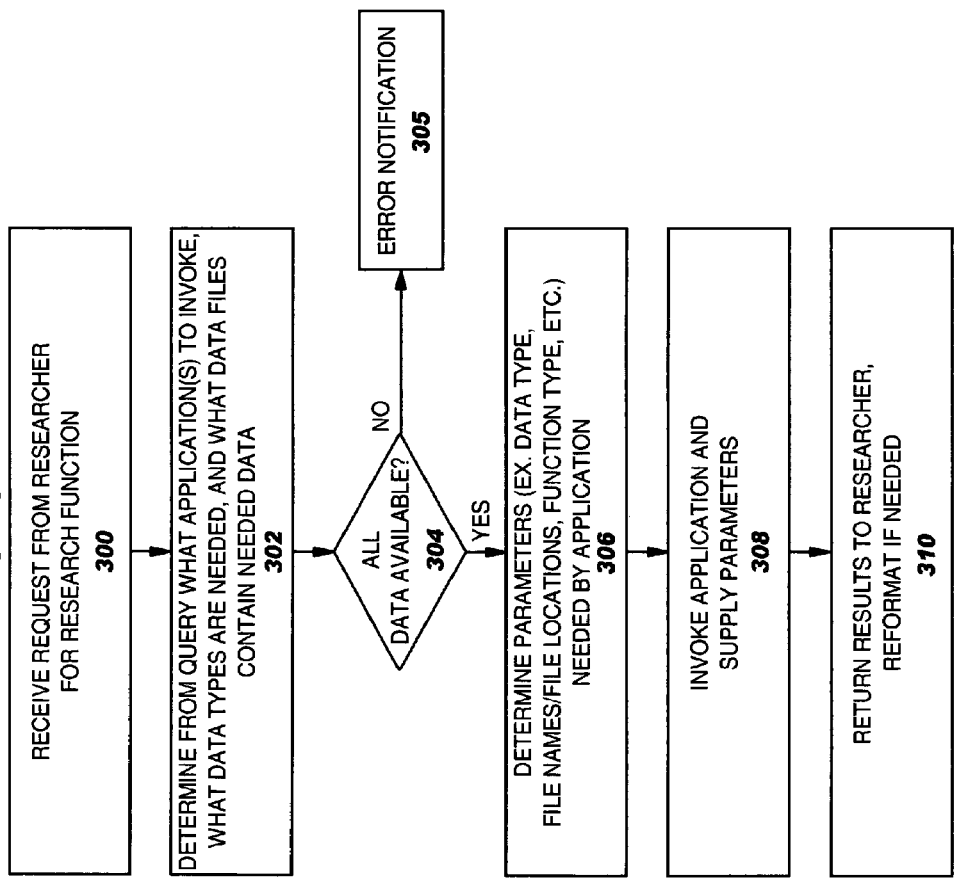
FIG. 9 is a flow chart showing function of a research data management program within an application server system of FIG. 1.

The data 24, 36 and 40 is automatically made available to the application server system 96, research application server 108 and post processor 100, which in the example of FIG. 8, have been consolidated into one server. These include a high performance computer system (HPCS) 292, and act on the data (as illustrated in FIG. 9). (The raw data 40 is provided to the application server system 96 via the preprocessor 92.) In a typical scenario, the research application server 108 and/or the application server system 96 would scan the reference microarray data repository for highly probable patterns. For example, a standard Hidden Markov algorithm in a data mining application 290 (within research application server 108) detects patterns ranked by their probabilities. Data mining application 290 then compares these patterns with the probable patterns detected in the clinical microarrays from the clinical samples. The concordance of these two types of data identifies what characteristic biomolecules are associated with a disease state. Next, a research application 282, 284 and/or 286 within the research application server 108 numerically compares biomolecular pathway data connecting differing biomolecules with the biomolecules identified from both sets of microarray data. This provides information on the disease mechanism, especially indicating related sets of biomolecules, any one of which may be targeted in treating a disease.

FIG. 8 also illustrates four types of end user researchers that use the processed output from the research application server 108, application server system 96 and post processor 100. Occasionally, the researchers will also access the raw data 40 as stored in data repositories 270, 272, 274 and 275. Each of these types of researchers interfaces to the application server system 96 via a research data management program 280. Research data management program 280 processes the queries made by the researches for different types of processed and raw data. In response, the research management program 280 invokes the corresponding applications 282, 284 and/or 286 and supplies them with the requisite query parameters and research data files in order to process the query and supply the researcher with the processed data in a form tailored to the type of researcher.

A microarray research technician 250 scans the output from the LIMS and the performance of the microarray instrumentation, for example by number of entries in the local repository or reference data repository. The research technician 250 also uses microarray pattern statistics output from the application server system 96. A molecular biologist researcher 252 obtains pattern and probability numerical values from the application server system 96, and then uses them to validate or extend the pathway data, using the identities of interacting biomolecules as obtained from the LIMS and external sources. A physician researcher 254 analyzes statistical correlation of microarray pattern probabilities with known disease states as a means of diagnosis and prognosis. Consequently, the physician uses primary trends and statistics of microarray patterns and clinical data output from the research application server 108 via the application server system 96 and access to the reference data repository of patterns generated by data mining application 290. A drug design researcher 256 uses clinical symptoms microarray statistics and their correlation with pathways output from research application server 108 via the application server system 96, and the following types of data output from the application server system 96: (a) names of biomolecules from clinical microarray data connected to disease state, (b) their probabilities of appearance in the microarrays (where these biomolecules have been identified using the reference data repository), and (c) probable molecular interactions to design a drug that will specifically interact with the molecules that support the disease. With this data, the pharmaceutical designer may then use standard drug design tools to develop a novel drug once these relevant biomolecule targets have been identified.

FIG. 9 illustrates the function of the research data management application 280 within the combined application server system 96, post processor 100 and research application server 108 in more detail. In step 300, research data management application 280 receives a data processing request from researcher 250, 252, 254 or 256. The request specifies one or more data processing functions to be performed by one or more of the research applications 282, 284 or 286. If more than one data processing function is needed, the request specifies the order of that the data processing functions should be performed. The request also specifies types of data processing results of interest, type or source of the research data that should be processed, and optionally, the age or range of data that should be used or that data should pass basic validity tests before being used. In response to the data processing request and based on tables, research data management application 280 determines what research application(s) 282, 284 and/or 286 are needed to perform the requested function, and the names of data files that contain the data needed to be processed by these research application(s) to return the processed data needed by the researcher (step 302). If the data processing request does not specify the type of data needed by the research application(s), the research data management application 280 consults a configuration file for the research application to determine the types of data needed for the research application to perform its function (step 302). Next, research data management application 280 determines if all of the data needed by the research application(s) to perform the requested function is available from data repositories within system 20 (decision 304). This determination is made by checking the data research files correlated to the requisite data types, to determine if they contain valid data within the data age range, if any, specified by the researcher's data processing request. If not, then the research data management application 280 sends an error message to the researcher (step 305). (In response, the researcher can change the age, range or type parameters, and submit another data processing request.) If so, the research data management application 280 determines the parameters needed by each research application to perform the requested function (step 306). These parameters include the names of the data files that contain the requisite data, the data age range, if any, for data to be processed, identifiers for the specific data items within the data files (such as molecule or molecule family names), and specification of the requested function or functions (if the research application is capable of performing more than one function). This determination is based on information in the researcher's data processing request and a table which lists which data files contain which types of data. Then, the research data management program 280 invokes the target research application(s) and supplies the requisite parameters in a function request (step 308). These parameters include the sequence in which the applications are to be performed (the sequence possibly being computed based on intermediate results and possibly including iteration), and data to control the operation of the application, such as minimal probabilities of sequences resulting from a Blast search to be retained for further analysis. In response, the research application(s) performs its function. When the research application(s) performs its function, it may query the data mining application 290 for pattern information and analysis, as needed. Also, if two or more research applications are invoked and executed, they may communicate with each other to collectively perform the requested function. After completing its processing, the research application(s) returns the results to the research data management program 280. As explained above, each item or data file may include an indication of the proper format of the report or processed data furnished to the researcher, based on a parameter specified in the researcher's function request. In such a case, the research data management program 280 will format the report or processed data accordingly (step 280). Then, the research data management program 280 returns the reformatted resultant data to the researcher that made the data processing request (step 310).

Figure 4A:
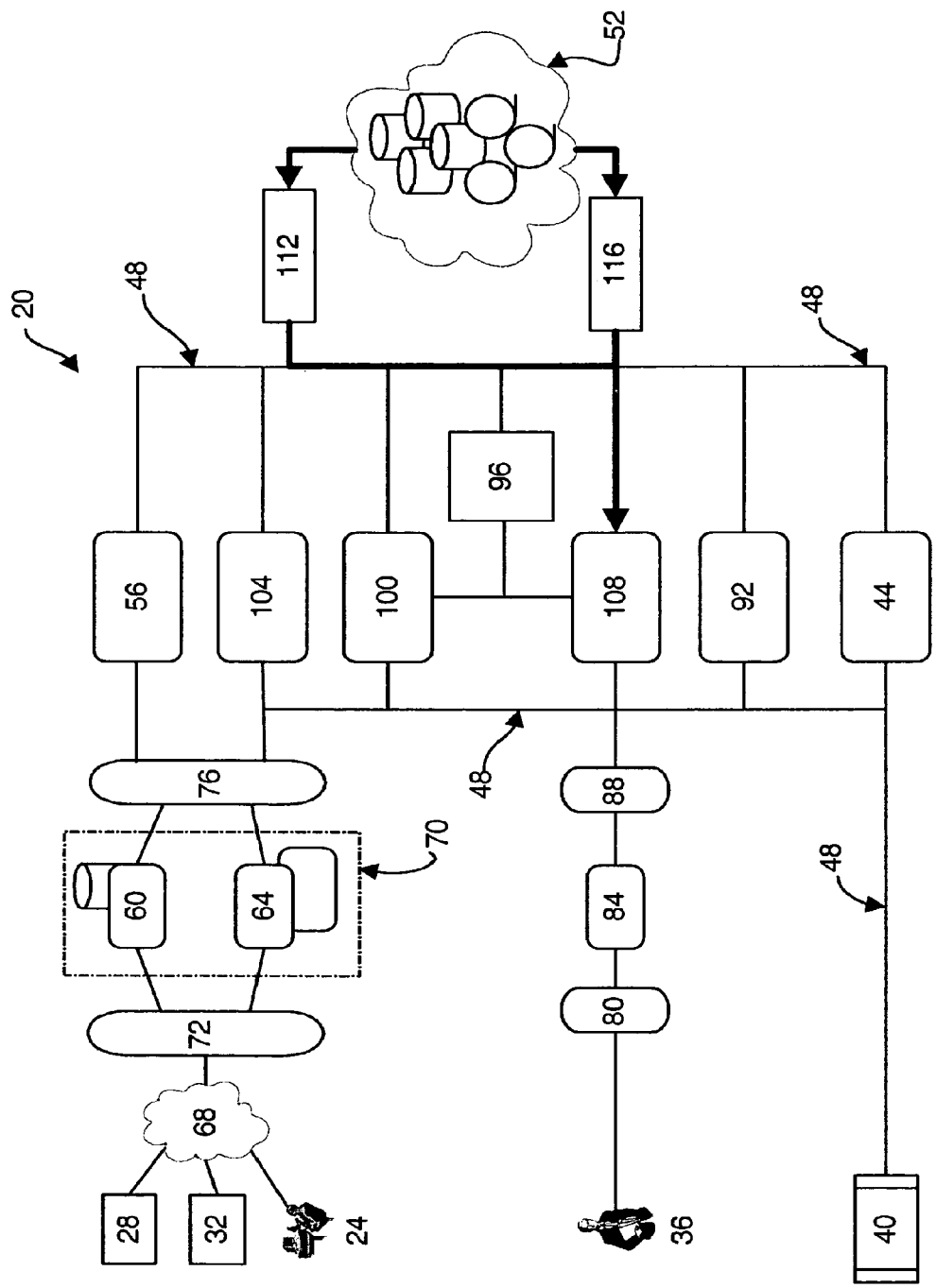
FIG. 4a shows control and data flows between components of the system of FIG. 1 when pattern matching and pattern recognition of experimental data.
Figure 4B:
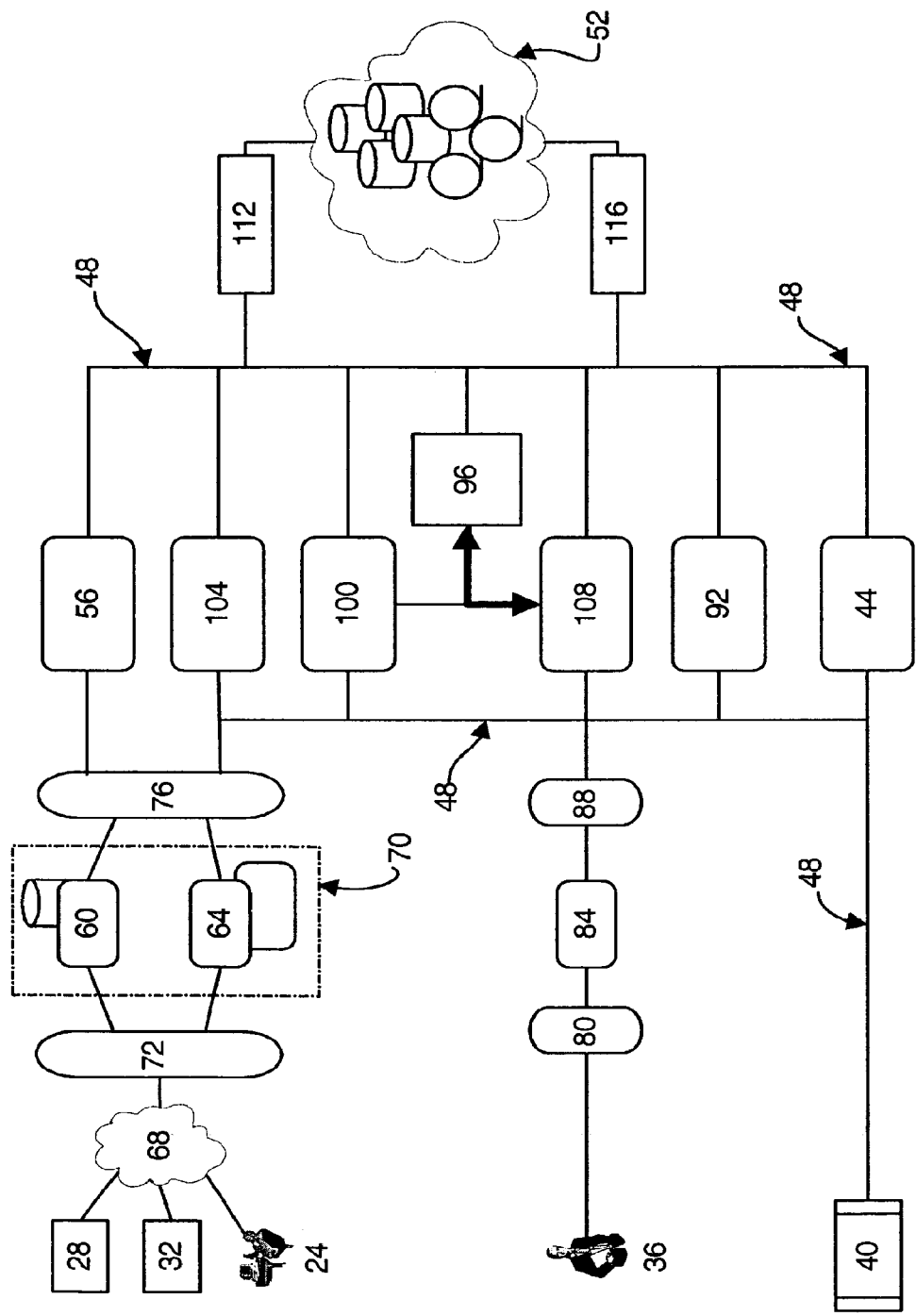
FIG. 4b shows control and data flows between components of the system of FIG. 1 when pattern matching and pattern recognition of experimental data.
Figure 4C:
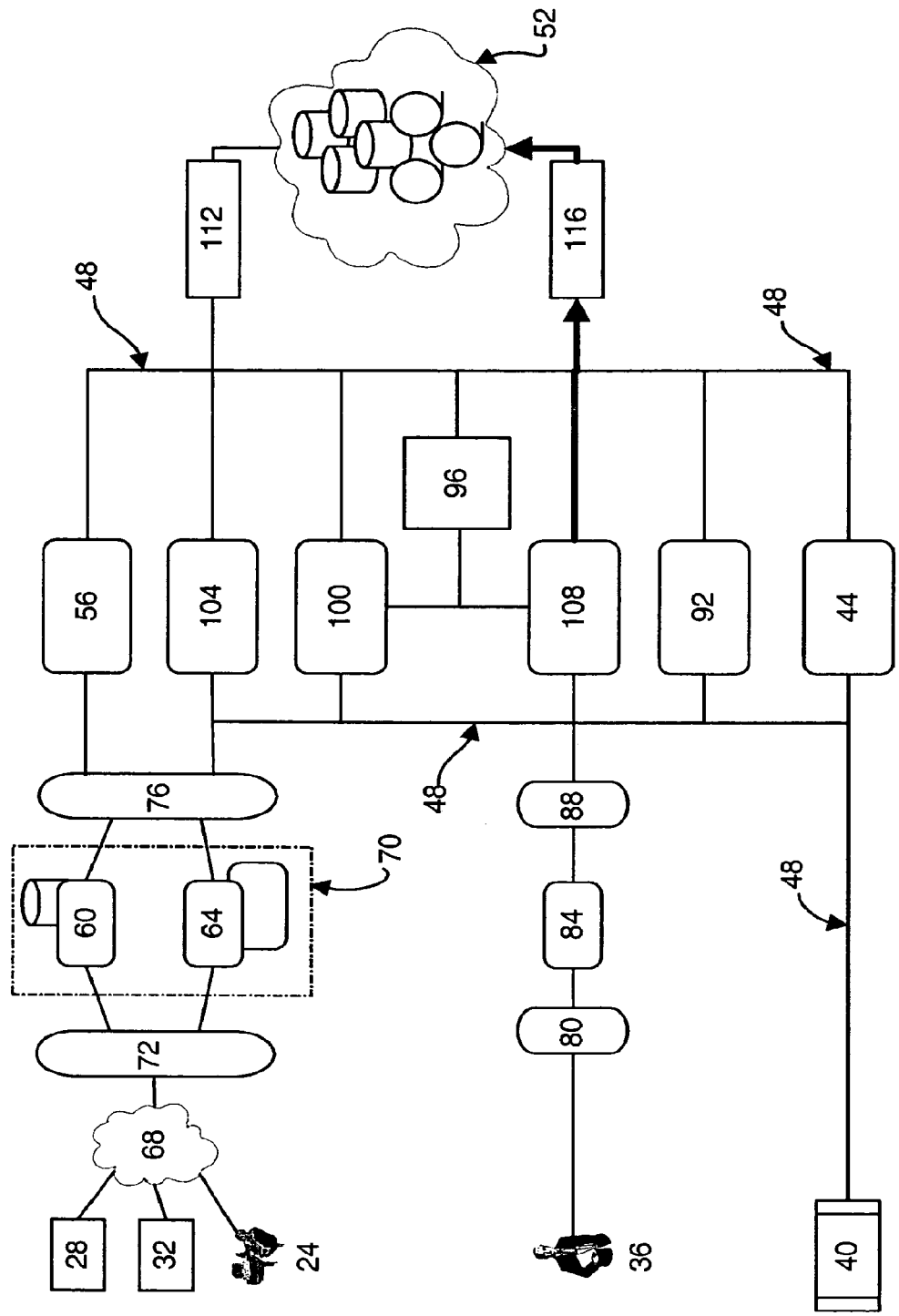
FIG. 4c shows control and data flows between components of the system of FIG. 1 when pattern matching and pattern recognition of experimental data.

One of the important activities in research programs is to compare experimental data to reference data, to interpret the experimental data to obtain results, and to store those results with the experimental data. FIGS. 4a, 4b and 4c show an example of such data "fitting" within system 20. It is assumed, for the purposes of this example, that the data fitting is performed through asynchronous interfaces/services as data fitting can be computationally complex and is typically implemented as a batch process which does not require user intervention. However, it is important to note that system 20 is not limited to such batch processes, and system 20 can support interactive data fitting and/or examination, such as by data visualization tools, etc. with researchers 36.

In FIG. 4a, reference data access server 112 provides RAS 108 with reference data from virtual storage device 52. This reference data will be used to interpret and analyze experimental data. Research data server 116 provides experimental data that has been appropriately preprocessed to RAS 108 from virtual storage device 52. Next, in FIG. 4b, RAS 108 employs computing services of application server system 96 to perform high speed pattern matching and recognition, or other techniques such as statistical analysis, etc. to best interpret the experimental data. Finally, as shown in FIG. 4c, the obtained results are stored in virtual storage device 52, via research data server 116.

Figure 5A:
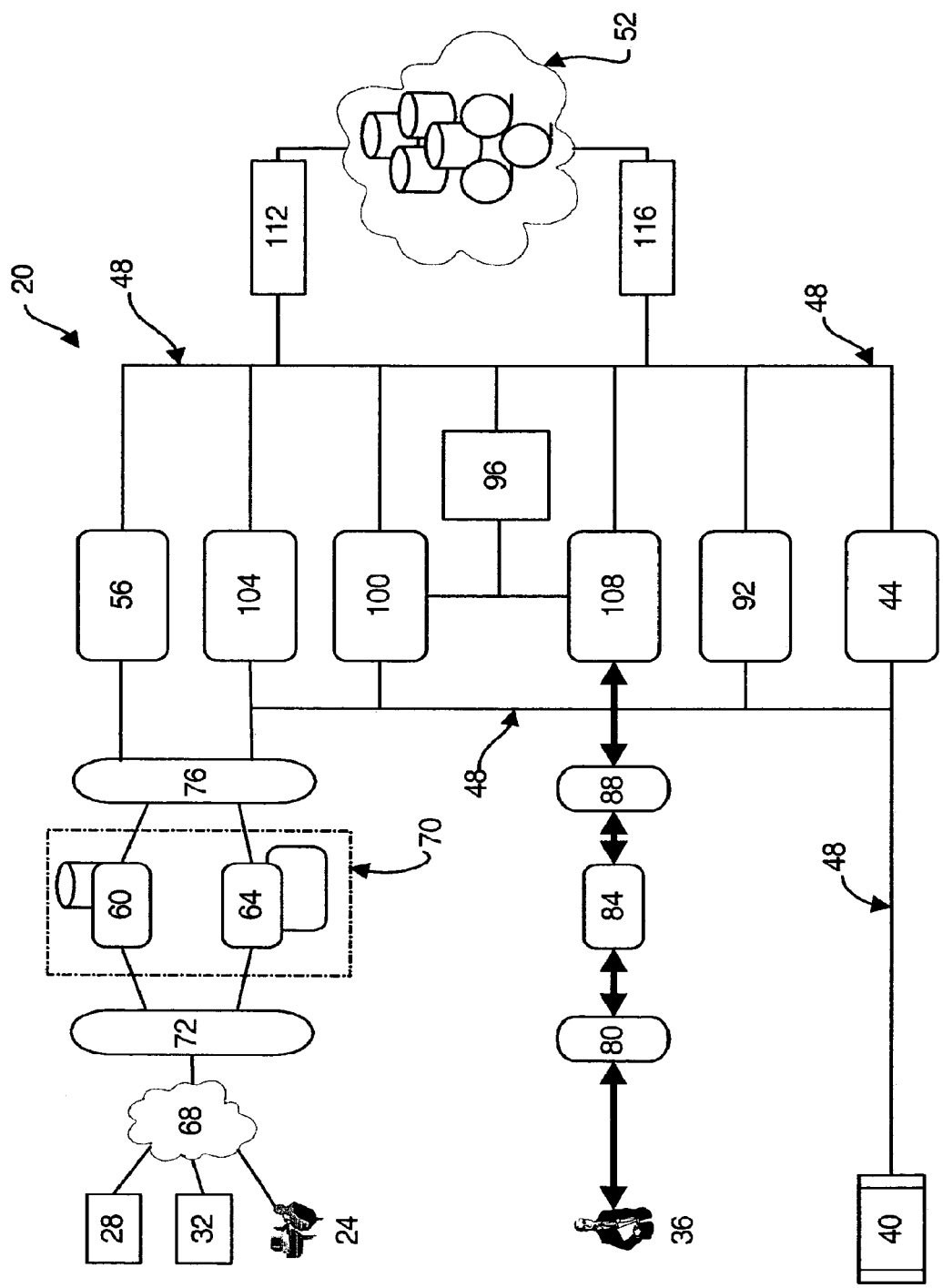
FIG. 5a shows control and data flows between components of the system of FIG. 1 when performing data analysis and/or result generation of experimental data.
Figure 5B:
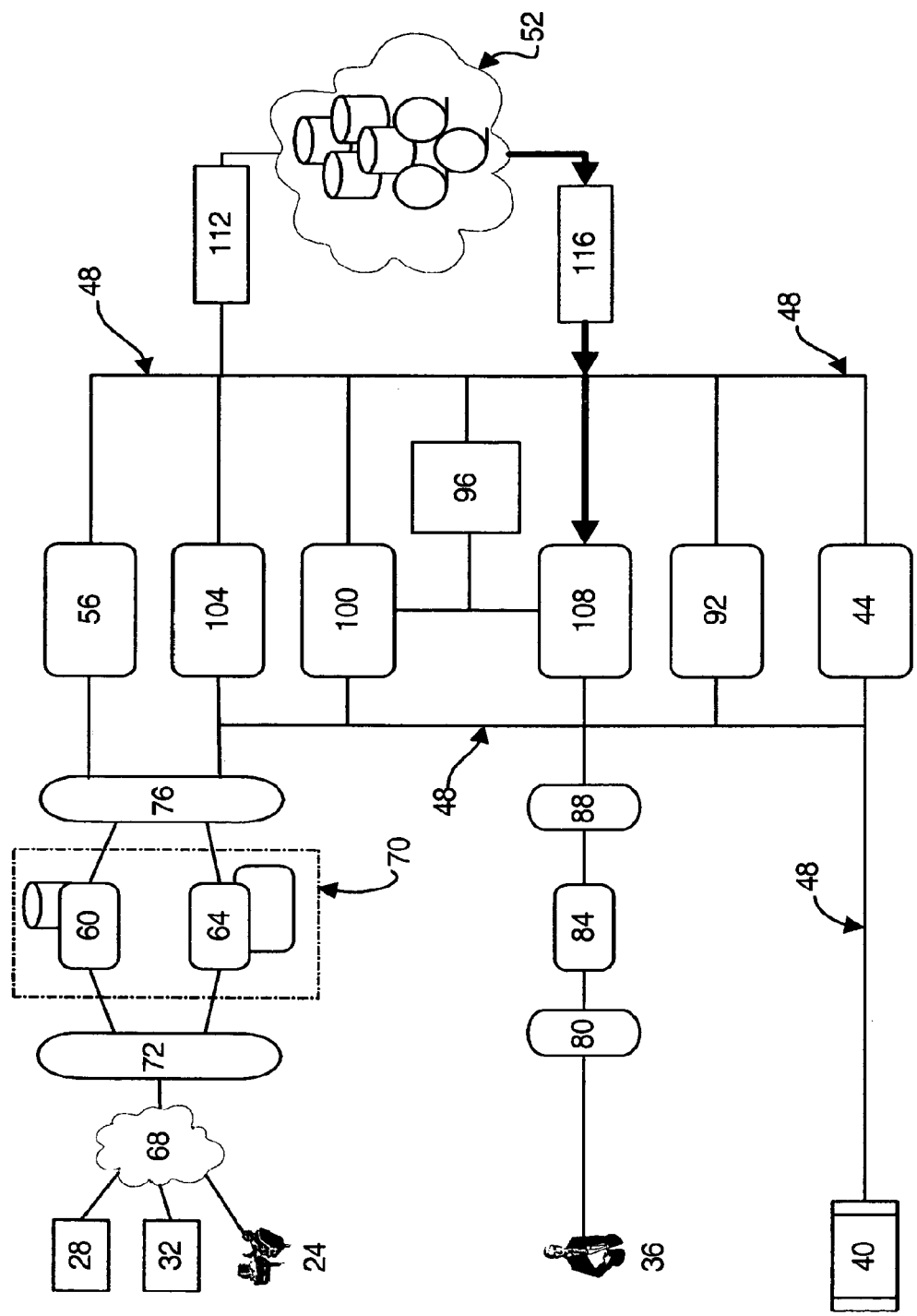
FIG. 5b shows control and data flows between components of the system of FIG. 1 when performing data analysis and/or result generation of experimental data.
Figure 5C:
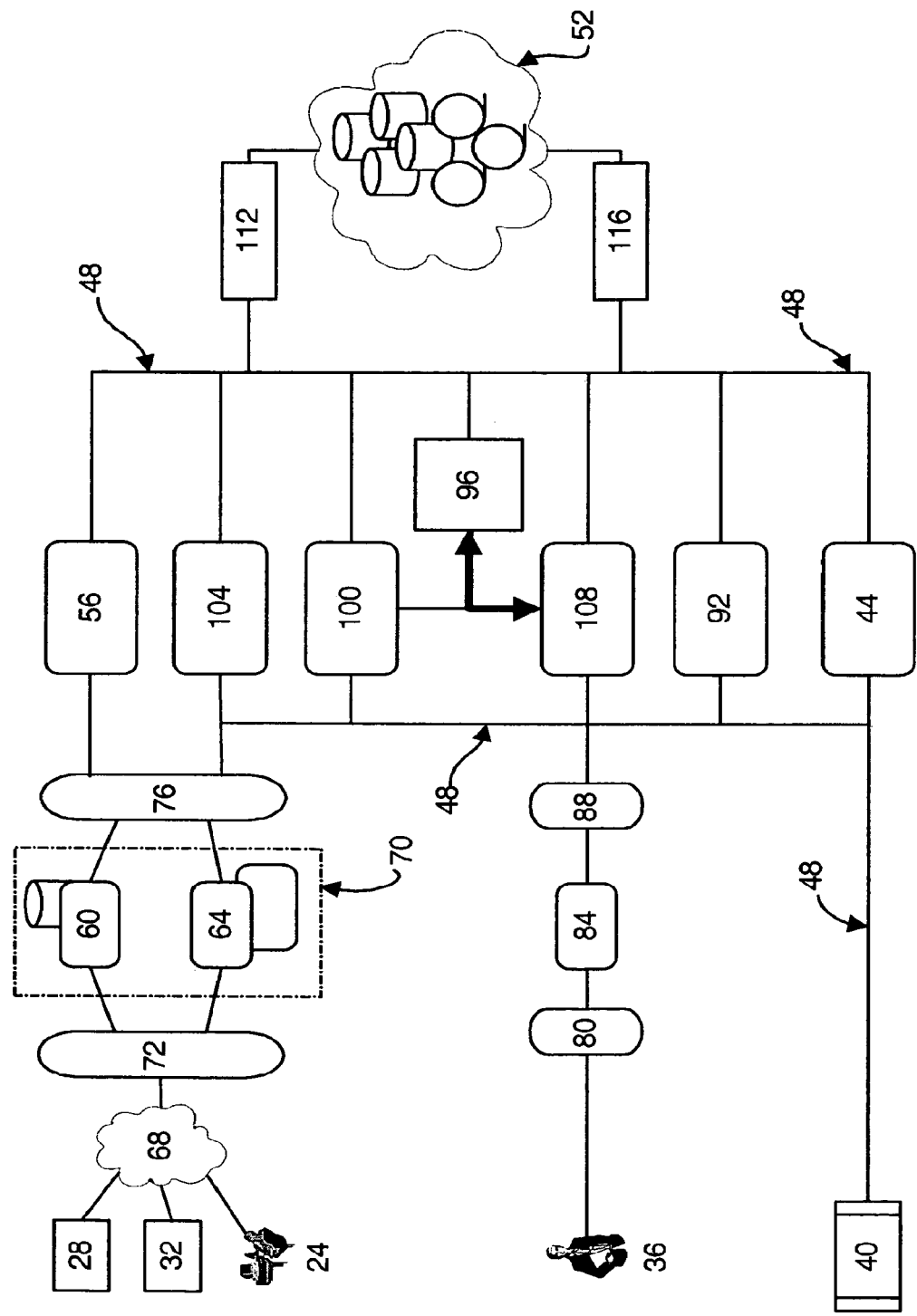
FIG. 5c shows control and data flows between components of the system of FIG. 1 when performing data analysis and/or result generation of experimental data.
Figure 5D:
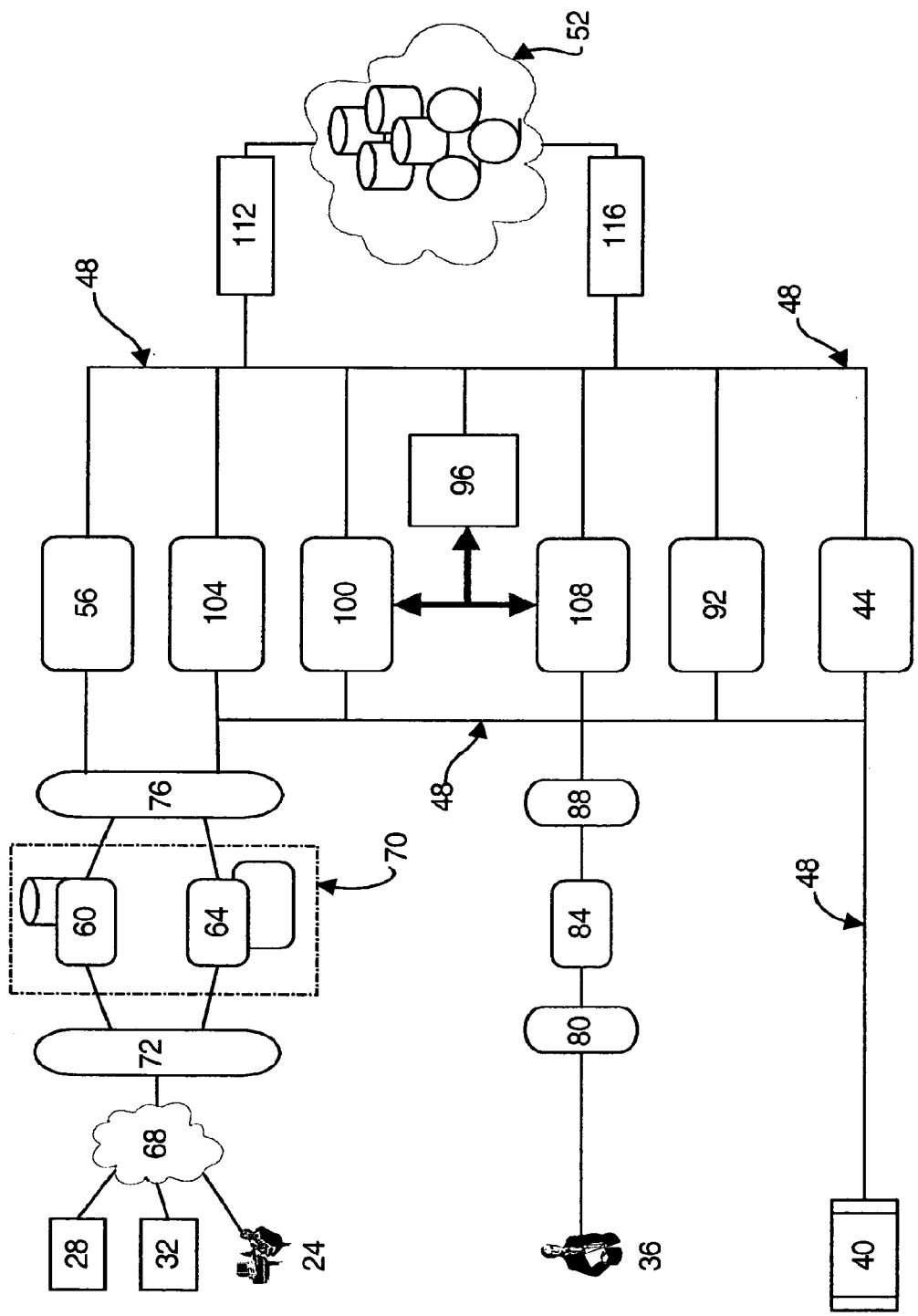
FIG. 5d shows control and data flows between components of the system of FIG. 1 when performing data analysis and/or result generation of experimental data.
Figure 5E:
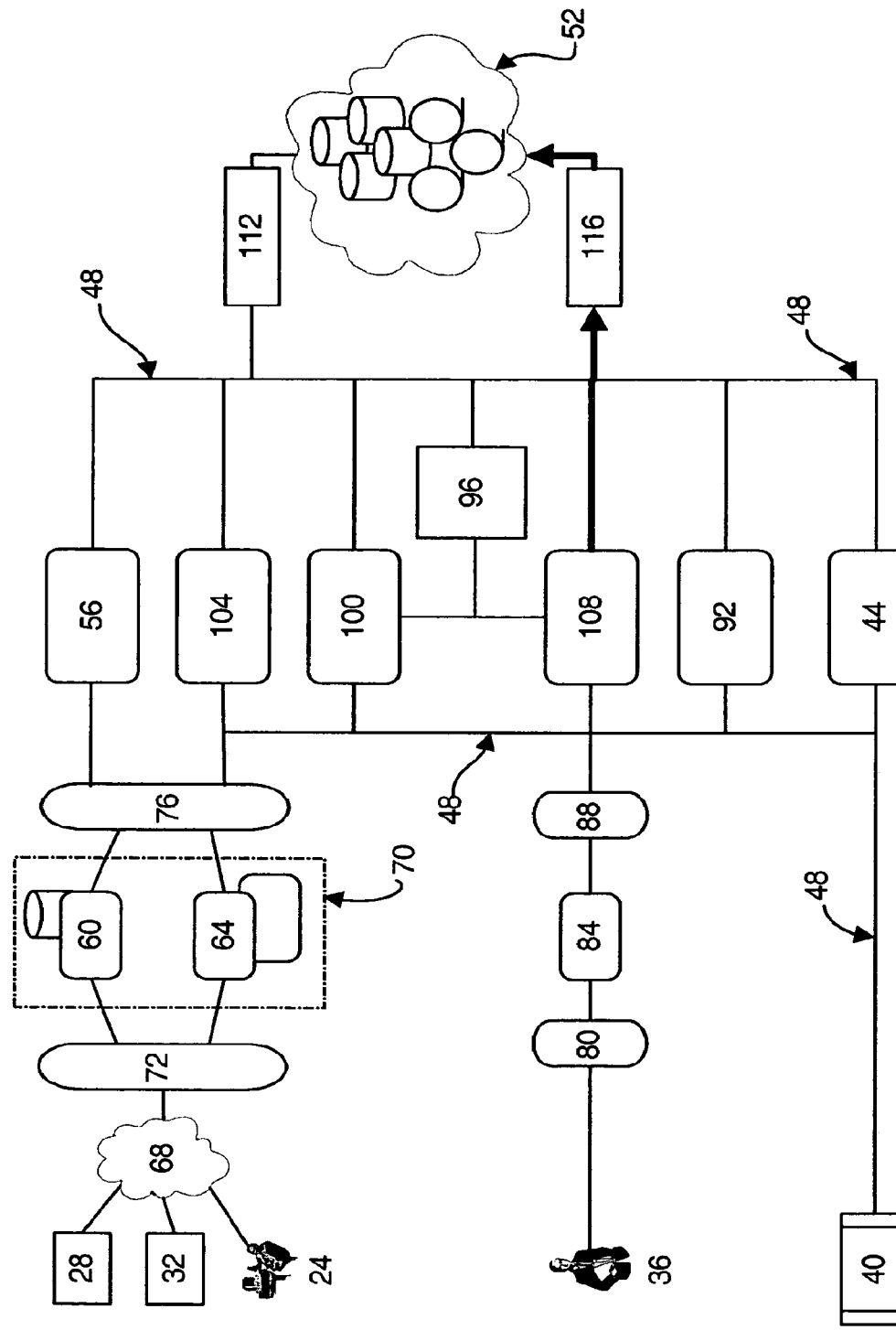
FIG. 5e shows control and data flows between components of the system of FIG. 1 when performing data analysis and/or result generation of experimental data.

Another important activity in research is the analysis of data and generation of results. An example of this activity, employing system 20, is shown in FIGS. 5a through 5e. In FIG. 5a, an internal researcher 36 employs a Web Browser interface, provided by web server 84, to interact with RAS 108. If researcher 36 determines that further analysis of a data set is merited, the data set to be analyzed is provided to RAS 108 from virtual storage device 52, via research data server 116, as shown in FIG. 5b. RAS 108 employs the HPCS to process the retrieved data set, using the analytic tools selected by researcher 36 via the Web Browser, as shown in FIG. 5c. If desired, or required, researcher 36 can have RAS 108 post process any results, via post processor 100 and the HPCS, as shown in FIG. 5d. The processed data, such as the conclusions, researcher annotations, etc. are then stored in virtual storage device 52, via research data server 116 with the original data sets as shown in FIG. 5e.

In some cases, the results of the research may be published to internal researchers 36 on the research team, and external researchers 24 and/or external databases. As used herein, the term "publishing" is intended to include the act of making information available for subsequent review, and this would include placing research results into a database which can be externally accessed, publishing scientific articles in journals, etc. and "pushing" results to researchers or institutions, etc. which have previously subscribed or otherwise indicated an interest in the results. Internal publishing can be synchronous, with internal researchers 36 accessing results and other information as it becomes available while external publication can be either synchronous, such as when an external researcher 24 accesses results through knowledge management server 104, or asynchronous such as when an external researcher 24 accesses an external replica of the published data held in an external database.

Figure 6A:
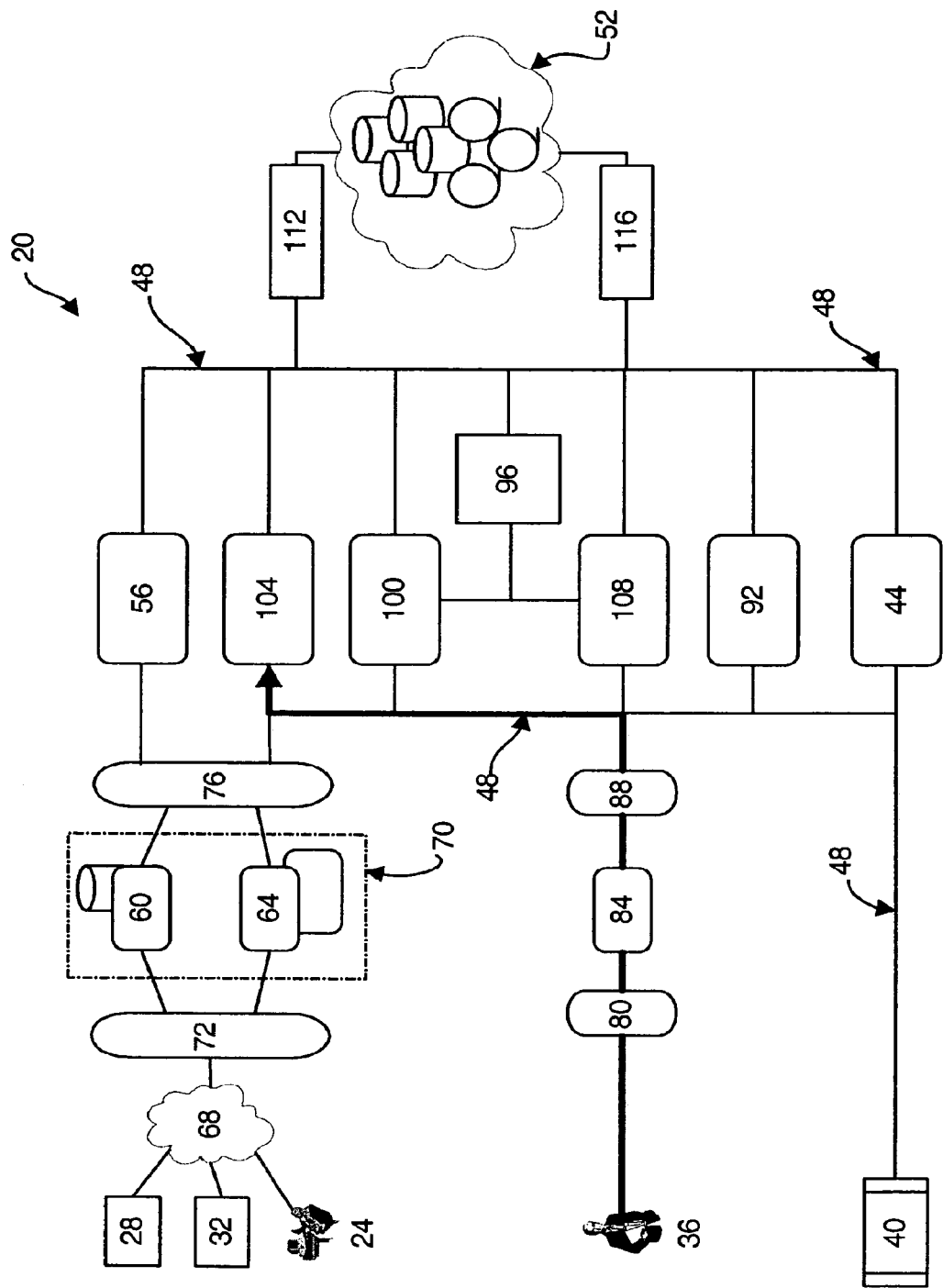
FIG. 6a shows control and data flows between components of the system of FIG. 1 when publishing results to an internal researcher.
Figure 6B:
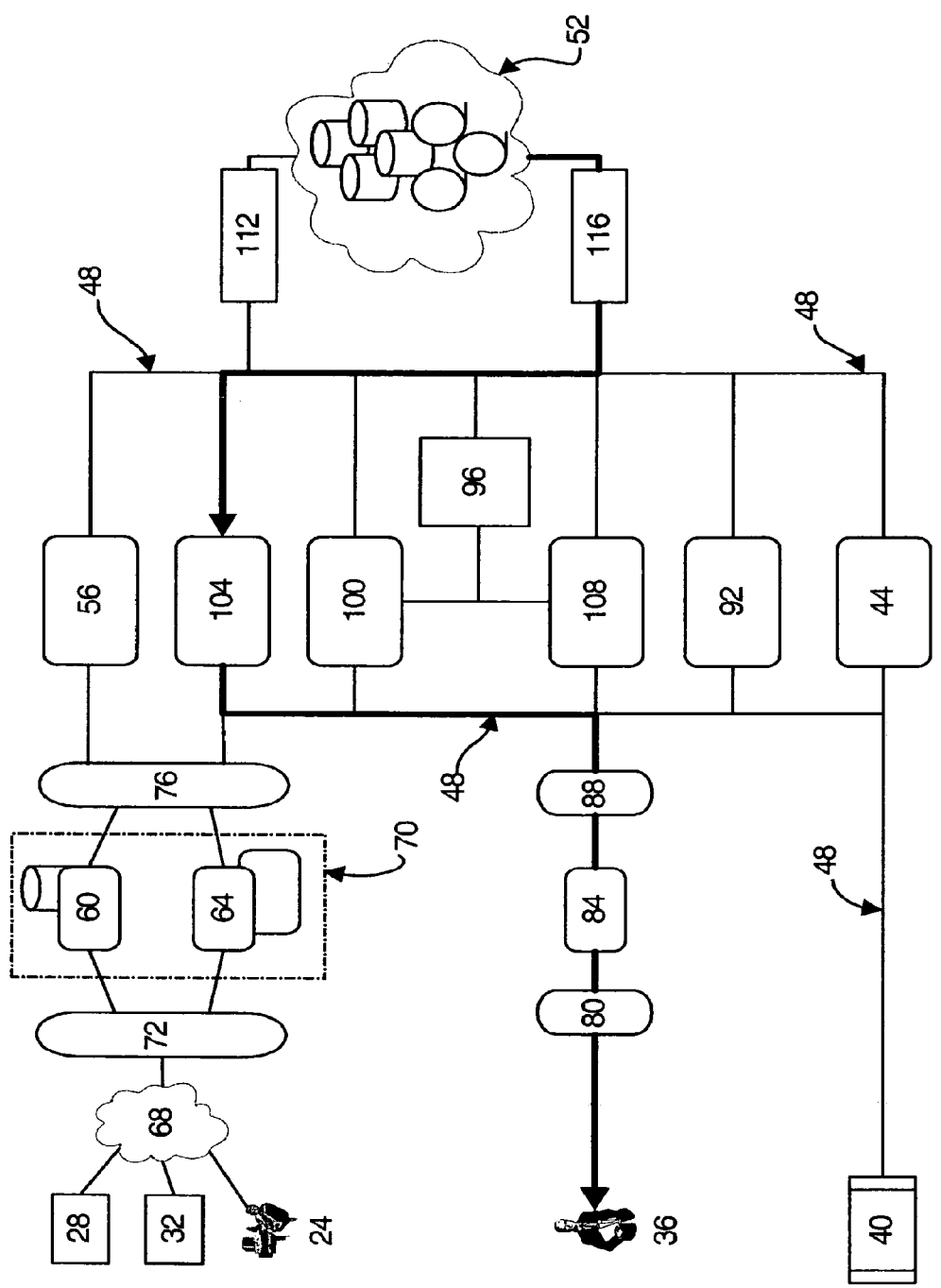
FIG. 6b shows control and data flows between components of the system of FIG. 1 when publishing results to an internal researcher.

FIGS. 6a, 6b, 7a and 7b show examples of the publishing of research results and other information with system 20. Publication to an internal researcher 36 is illustrated in FIG. 6a, wherein researcher 36 uses a web browser to access a Web Browser via the web server 84, to interface with knowledge management server 104. KMS 104 has access to all federated information and results, the federated information and results being appropriately indexed, in virtual storage device 52 and throughout system 20. As internal researcher 36 commences his or her interaction with KMS 104, the security management services authenticate the authority of the internal researcher to access the results and/or any research applications internal researcher 36 requests. FIG. 6b shows the requested results being provided to internal researcher 36.

Figure 7A:
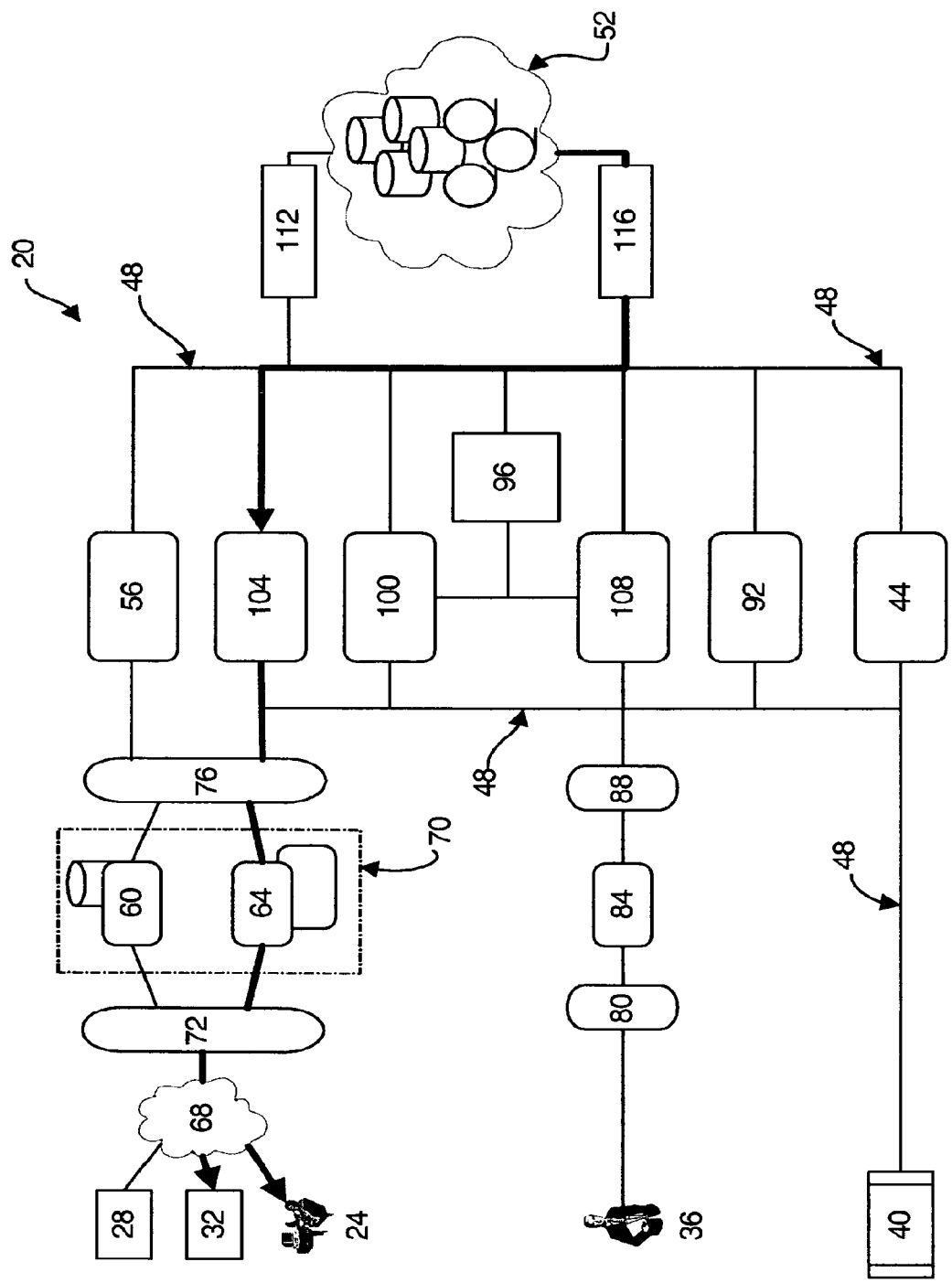
FIG. 7a shows control and data flows between components of the system of FIG. 1 when publishing results to an external researcher or external sites.
Figure 7B:
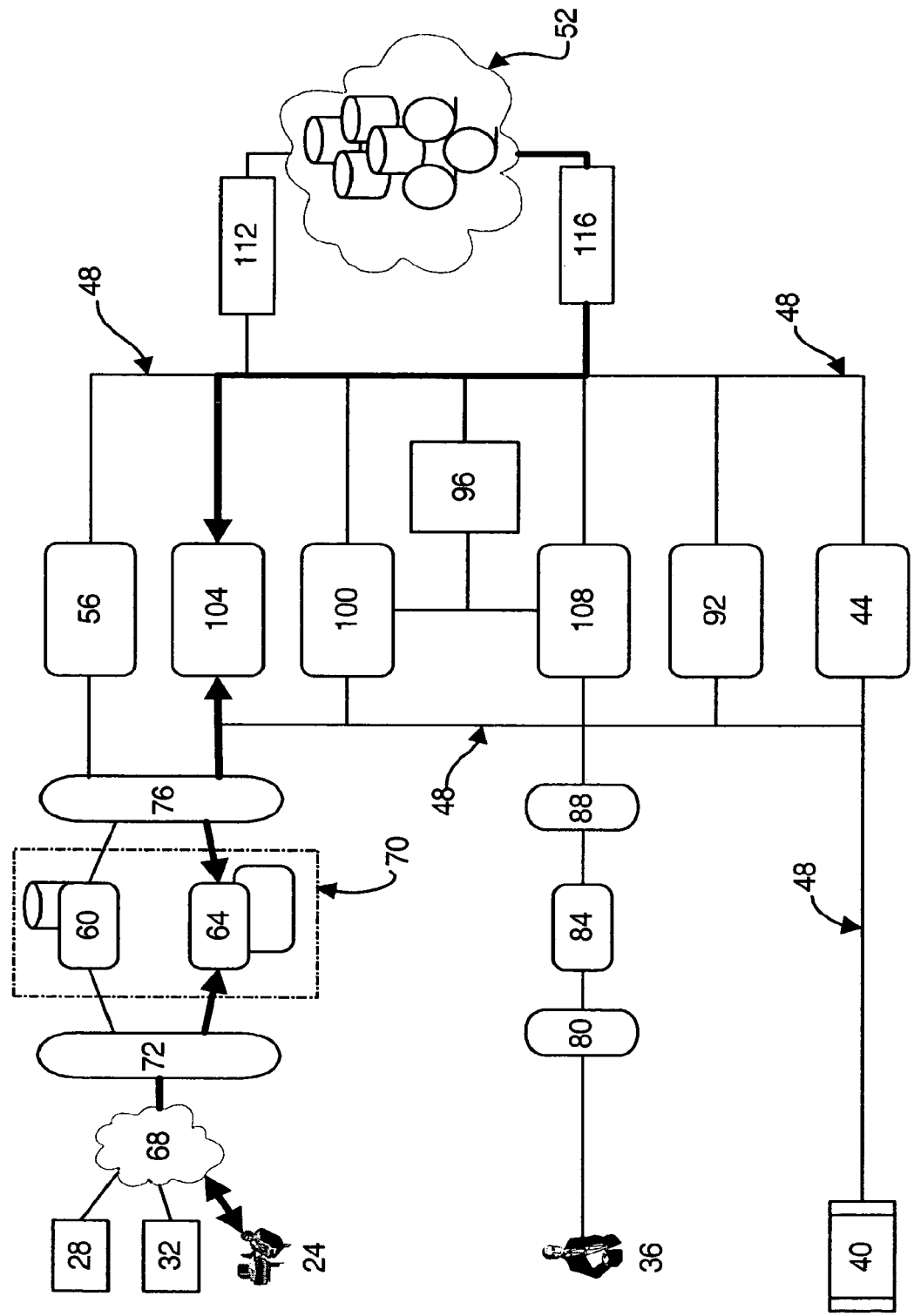
FIG. 7b shows control and data flows between components of the system of FIG. 1 when publishing results to an external researcher or external sites.

In FIG. 7a, an example of an asynchronous "push" of results is shown. In this example, an external researcher 24 or other external data user, such as a public or commercial database, has previously indicated an interest in research results and this interest has been authenticated and approved by the above-described security management services. Accordingly, when KMS 104 determines that results or information are available in virtual storage device 52, via research data server 116, are to be pushed to an external researcher 24 or external database, the results are packaged by KMS 104 and forwarded to the appropriate external destination via B2B server 64. In FIG. 7b, an external researcher 24 interfaces with KMS 104 in a synchronous manner, much like an internal researcher would, via B2B server 64. In this case, the above-described security management services authenticate the external researcher 24 and, on an ongoing basis, ensure the researcher's authority to access requested information. KMS 104 retrieves properly requested information from virtual storage device 52, via research data server 116, and provides it to the external researcher 24 via B2B server 64.

As will now be apparent, the present invention provides an end to end information technology system to allow researchers from multiple disciplines and in geographically diverse locations to cooperate in research efforts. Management of large amounts of experimental and reference information is provided to meet diverse researcher and regulatory requirements, while appropriate security of the managed information is maintained.

The above-described embodiments of the invention are intended to be examples of the present invention and alterations and modifications may be effected thereto, by those of skill in the art, without departing from the scope of the invention which is defined solely by the claims appended hereto.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A computer system for processing a request by a researcher to perform a data processing function, the computer system comprising:
   one or more processors, one or more computer-readable memories, one or more computer-readable tangible storage devices, and program instructions stored on at least one of the one or more storage devices for execution by at least one of the one or more processors via at least one of the one or more memories, the program instructions comprising:
   first program instructions to receive a request to perform research, the request specifying a plurality of types of data processing functions needed for the research, an order to perform the plurality of types of data processing functions, a type of data processing results for the research, a type of research data that should be processed, and a data range of the research data to be processed;
   second program instructions, responsive to the request and the specified plurality of types of data processing functions, the order to perform the plurality of types of data processing functions, the type of data processing results and the type of research data that should be processed, for determining a plurality of processing applications, not identified in the request, to perform the requested research, determining application parameters, and determining identities of data files that contain information needed by the plurality of processing applications to perform the requested research; and
   third program instructions to invoke the plurality of processing applications and supply to the plurality of processing applications (a) an identification of the plurality of types of data processing functions, (b) the application parameters, (c) the identities of data files that contain information needed by the plurality of processing applications to perform the requested research, and (d) a data range of the research data, the plurality of processing applications performing the plurality of data processing functions in the requested order using data within the data range of the research data, generating a report having resultant data with a type corresponding to the request, comparing the research data to existing research data and determining the quality of the research data based on the comparison of the data to existing research data;
   and wherein the first, second and third program instructions are stored on the one or more computer-readable tangible storage devices.

2. The system of claim 1 further comprising fourth program instructions to automatically obtain the information for the data files and automatically update the information for the data files as new data for the data files becomes available; and the fourth program instructions being stored on the one or more computer-readable tangible storage devices.

3. The system of claim 1 wherein the request specifies the date range of the research data from the request that should be processed, and the third program instructions to invoke and supply supplies the date range of the research data from the request to the subset of processing applications to perform the type of data processing function using data within the date range of the research data from the request to yield the type of data processing results.

4. The system of claim 1 wherein the request specifies the range of research data parameters other than time oriented parameters that should be processed, and the third program instructions to invoke and supply supplies the range of research data parameters other than time oriented parameters to the subset of processing applications to perform the type of data processing function using data having the range of research data parameters other than time oriented parameters to yield the type of data processing results.

5. The system of claim 1 wherein the type of data processing function is for life sciences research.

6. The system of claim 1 wherein the third program instructions to invoke and supply further include determining whether the data files contain valid data within the data range.

7. The system of claim 1 wherein second program instructions to determine application parameters further include determining application parameters based, in part, on the request; and the application parameters including identifiers for data items within the data files.

8. A computer program product for managing a request by a researcher to perform a data processing function, the computer program product comprising:
   one or more computer-readable tangible storage devices and program instructions stored on at least one of the one or more storage devices, the program instructions comprising:
   first program instructions to receive a request to perform a type of data processing function for research, the request specifying the type of the data processing function, a type of data processing results, a type of research data that should be processed, and a date range of the research data from a date of the request that should be processed, the request not identifying any processing application to perform the data processing function;

second program instructions, responsive to the request and based on the type of data processing function, the type of data processing results of interest to the researcher and the type of research data that should be processed, to determine a subset of processing applications to perform the type of data processing function to yield the type of data processing results and determining application parameters needed by the subset of processing applications to perform the type of data processing function to yield the type of data processing results; and third program instructions to invoke the subset of processing applications and supply to the subset of processing applications (a) an identification of the type of data processing function, (b) the application parameters needed by the subset of processing applications to perform the type of data processing function to yield the type of data processing results (c) the date range of the research data from a date of the request, such that the subset of processing applications can perform the specified data processing function using data within the date range of research data from the request, generating a report having resultant data corresponding to the request, the report being formatted based on the request, comparing the research data to existing research data and determining the quality of the research data based on the comparison of the data to existing research data; and wherein the first, second and third program instructions are stored on the one or more computer-readable tangible storage devices.

9. The computer program product of claim 8 further comprising fourth program instructions to automatically obtain the information for the data files and automatically update the information for the data files as new data for the data files becomes available; and wherein the fourth program instructions are stored on the one or more computer-readable tangible storage devices.

10. The computer program product of claim 9 wherein second program instructions to determine application parameters further include determining application parameters based, in part, on the request; and the application parameters including identifiers for data items within the data files.

11. The computer program product of claim 10 wherein the type of data processing function is for life sciences research.

12. The computer program product of claim 11 wherein the third programming instructions to invoke and supply further include determining whether the data is within the date range of research of research data.

13. A computer program product for managing a request by a researcher to perform a data processing function, the computer program product comprising:

one or more computer-readable tangible storage devices and program instructions stored on at least one of the one or more storage devices, the program instructions comprising:

first program instructions to receive a request to perform a type of data processing function for research, the request specifying the type of the data processing function, a type of data processing results, a type of research data that should be processed, a date range of the research data from a date of the request that should be processed, the request not identifying any processing application to perform the data processing function;

second program instructions, responsive to the request and based on the type of data processing function, the type of data processing results and the type of research data that should be processed, to determine a subset of processing applications to perform the type of data processing function to yield the type of data processing results, and determine application parameters and identities of data files that contain information needed by the subset of processing applications to perform the type of data processing function to yield the type of data processing results; and third program instructions to invoke the subset of processing applications and supply to the subset of processing applications (a) an identification of the type of data processing function, (b) the identities of data files that contain information needed by the subset of processing applications to perform the type of data processing function to yield the type of data processing results, (c) the date range of the research data from a date of the request and (d) the application parameters, such that the subset of processing applications can perform the specified data processing function using data having the range of research data, generating a report having resultant data corresponding to the request, the report being formatted based on the request, comparing the research data to existing research data and determining the quality of the research data based on the comparison of the data to existing research data; and wherein the first, second and third program instructions are recorded on the one or more computer-readable tangible storage devices.

14. The computer program product of claim 13 further comprising fourth program instructions to automatically obtain the information for the data files and automatically update the information for the data files as new data for the data files becomes available; and wherein the fourth program instructions are stored on the one or more computer-readable tangible storage devices.

15. The computer program product of claim 13 wherein the type of data processing function is for life sciences research.

16. The computer program product of claim 13 wherein the second program instructions to determine application parameters further includes determining application parameters based, in part, on the request; and the application parameters including identifiers for data items within the data files.

17. The computer program product of claim 16, wherein the third programming instructions to invoke and supply further include determining whether the data files contain valid data within the data range of research data.

* * * * *